US007817276B2

(12) United States Patent
Kiesel et al.

(10) Patent No.: US 7,817,276 B2
(45) Date of Patent: Oct. 19, 2010

(54) DISTINGUISHING OBJECTS

(75) Inventors: Peter Kiesel, Palo Alto, CA (US); Oliver Schmidt, Palo Alto, CA (US); Michael Bassler, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 375 days.

(21) Appl. No.: 11/702,328

(22) Filed: Feb. 5, 2007

(65) Prior Publication Data

US 2008/0186488 A1   Aug. 7, 2008

(51) Int. Cl.
*G01N 21/55* (2006.01)
*G01N 21/00* (2006.01)
*G01B 9/02* (2006.01)
*G01J 1/42* (2006.01)

(52) U.S. Cl. ............... 356/436; 356/244; 356/517; 356/519; 250/208.2

(58) Field of Classification Search ............ 356/36–39, 356/432–444, 246, 417, 419, 519, 454, 410, 356/411; 250/208.2, 226, 578.1; 422/119; 436/172, 106, 164; 372/21–23
See application file for complete search history.

(56) References Cited

U.S. PATENT DOCUMENTS

| 3,915,573 A | | 10/1975 | Knoll et al. |
| 4,427,296 A | * | 1/1984 | Demarest et al. ............ 356/640 |
| 4,455,089 A | | 6/1984 | Yeung et al. |
| 4,573,796 A | | 3/1986 | Martin et al. |
| 4,820,042 A | * | 4/1989 | Barger ........................ 356/153 |
| 5,144,498 A | | 9/1992 | Vincent |
| 5,243,614 A | | 9/1993 | Wakata et al. |
| 5,312,535 A | * | 5/1994 | Waska et al. ................ 204/603 |
| 5,370,842 A | | 12/1994 | Miyazaki et al. |

(Continued)

FOREIGN PATENT DOCUMENTS

WO    WO 99/54730    10/1999

(Continued)

OTHER PUBLICATIONS

Vollmer, F., Arnold, S., Braun, D., Teraoka, I., Libchaber, A., "Multiplexed DNA Quantification by Spectroscopic Shift of Two Microsphere Cavities," Biophysical Journal, vol. 85, Sep. 2005, pp. 1-6.

(Continued)

*Primary Examiner*—Sang Nguyen

(57) ABSTRACT

While objects travel through an optical cavity, the cavity provides output light that is affected by the objects, causing the output light to have a varying intensity function. The output light is photosensed to obtain sensing results that depend on the varying intensity function. The sensing results are used to distinguish at least one object, such as from its environment or from objects of other types. The objects can, for example, be particles or biological cells, and their optical characteristics, such as refractive index or absorption, can affect the output light, so that information about them is included in the output light. The output light can, for example, have a laterally varying intensity function with peaks whose features change due to the objects. The sensing results can also be used to track objects, together with other information, such as about the speed of a fluid that carries the objects through the cavity.

39 Claims, 16 Drawing Sheets

U.S. PATENT DOCUMENTS

| | | | |
|---|---|---|---|
| 5,394,244 A | 2/1995 | Tsai | |
| 5,414,508 A | 5/1995 | Takahashi et al. | |
| 5,437,840 A * | 8/1995 | King et al. | 422/82.08 |
| 5,572,328 A | 11/1996 | Fouckhardt et al. | |
| 5,682,038 A | 10/1997 | Hoffman | |
| 5,760,900 A | 6/1998 | Ito et al. | |
| 5,784,507 A | 7/1998 | Holm-Kennedy et al. | |
| 5,793,485 A * | 8/1998 | Gourley | 356/318 |
| 5,880,474 A | 3/1999 | Norton et al. | |
| 5,945,676 A * | 8/1999 | Khalil et al. | 250/339.12 |
| 5,982,478 A | 11/1999 | Ainsworth et al. | |
| 5,982,534 A * | 11/1999 | Pinkel et al. | 359/387 |
| 6,049,727 A | 4/2000 | Crothall | |
| 6,091,502 A | 7/2000 | Weigl et al. | |
| 6,108,463 A | 8/2000 | Herron et al. | |
| 6,187,592 B1 | 2/2001 | Gourley | |
| 6,192,168 B1 | 2/2001 | Feldstein et al. | |
| 6,429,022 B1 | 8/2002 | Kunz et al. | |
| 6,459,080 B1 | 10/2002 | Yin et al. | |
| 6,483,959 B1 | 11/2002 | Singh et al. | |
| 6,490,034 B1 | 12/2002 | Woias et al. | |
| 6,580,507 B2 | 6/2003 | Fry et al. | |
| 6,639,679 B2 | 10/2003 | Frojdh | |
| 6,697,542 B2 * | 2/2004 | Platzman et al. | 385/5 |
| 6,768,555 B2 | 7/2004 | Chen et al. | |
| 6,795,190 B1 | 9/2004 | Paul et al. | |
| 6,839,140 B1 * | 1/2005 | O'Keefe et al. | 356/436 |
| 6,865,198 B2 * | 3/2005 | Taubman | 372/29.023 |
| 6,867,868 B1 | 3/2005 | Barbarossa | |
| 6,887,713 B2 | 5/2005 | Nelson et al. | |
| 6,906,792 B2 | 6/2005 | Ortyn et al. | |
| 6,934,435 B2 | 8/2005 | Kane | |
| 7,046,357 B2 | 5/2006 | Weinberger et al. | |
| 7,064,836 B2 | 6/2006 | Bechtel et al. | |
| 7,130,321 B2 * | 10/2006 | Spinelli et al. | 372/22 |
| 7,149,396 B2 | 12/2006 | Schmidt et al. | |
| 7,248,361 B2 | 7/2007 | Kiesel et al. | |
| 7,259,856 B2 * | 8/2007 | Kachanov et al. | 356/437 |
| 7,268,868 B2 | 9/2007 | Kiesel et al. | |
| 7,277,569 B2 * | 10/2007 | Bruce et al. | 382/133 |
| 7,291,824 B2 | 11/2007 | Kiesel et al. | |
| 7,305,112 B2 * | 12/2007 | Curry et al. | 382/133 |
| 7,310,153 B2 | 12/2007 | Kiesel et al. | |
| 7,315,667 B2 | 1/2008 | Schmidt et al. | |
| 7,358,476 B2 | 4/2008 | Kiesel et al. | |
| 7,386,199 B2 | 6/2008 | Schmidt et al. | |
| 7,387,892 B2 | 6/2008 | Kiesel et al. | |
| 7,391,517 B2 * | 6/2008 | Trebbia et al. | 356/432 |
| 7,420,677 B2 | 9/2008 | Schimdt et al. | |
| 7,433,552 B2 | 10/2008 | Kiesel et al. | |
| 7,440,101 B2 | 10/2008 | Auer et al. | |
| 7,466,409 B2 | 12/2008 | Scherer et al. | |
| 7,471,399 B2 | 12/2008 | Kiesel et al. | |
| 7,479,625 B2 | 1/2009 | Kiesel et al. | |
| 7,502,123 B2 | 3/2009 | Kiesel et al. | |
| 7,522,786 B2 | 4/2009 | Kiesel et al. | |
| 7,545,513 B2 | 6/2009 | Kiesel et al. | |
| 7,547,904 B2 | 6/2009 | Schmidt et al. | |
| 7,554,673 B2 | 6/2009 | Kiesel et al. | |
| 7,633,629 B2 | 12/2009 | Kiesel et al. | |
| 2003/0020915 A1 | 1/2003 | Schueller et al. | |
| 2003/0137672 A1 | 7/2003 | Moriya et al. | |
| 2003/0189711 A1 | 10/2003 | Orr et al. | |
| 2003/0235924 A1 | 12/2003 | Adams et al. | |
| 2004/0031684 A1 | 2/2004 | Witt | |
| 2004/0038386 A1 | 2/2004 | Zesch et al. | |
| 2004/0067167 A1 | 4/2004 | Zhang et al. | |
| 2004/0223135 A1 | 11/2004 | Ortyn et al. | |
| 2005/0042615 A1 | 2/2005 | Smith et al. | |
| 2005/0084203 A1 | 4/2005 | Kane | |
| 2005/0099624 A1 | 5/2005 | Staehr et al. | |
| 2005/0128479 A1 | 6/2005 | Gilbert et al. | |
| 2005/0158868 A1 | 7/2005 | Trebbia et al. | |
| 2005/0162648 A1 | 7/2005 | Auer et al. | |
| 2005/0164320 A1 | 7/2005 | McDevitt et al. | |
| 2005/0249605 A1 | 11/2005 | Kane et al. | |
| 2006/0039009 A1 | 2/2006 | Kiesel et al. | |
| 2006/0046312 A1 | 3/2006 | Kiesel et al. | |
| 2006/0121555 A1 | 6/2006 | Lean | |
| 2006/0182659 A1 | 8/2006 | Unlu et al. | |
| 2006/0193550 A1 | 8/2006 | Wawro et al. | |
| 2006/0268260 A1 | 11/2006 | Liu et al. | |
| 2006/0274313 A1 | 12/2006 | Gilbert et al. | |
| 2007/0009380 A1 | 1/2007 | Cunningham | |
| 2007/0070347 A1 | 3/2007 | Scherer | |
| 2007/0076210 A1 | 4/2007 | Kiesel et al. | |
| 2007/0116609 A1 | 5/2007 | Baeuerle et al. | |
| 2007/0146704 A1 | 6/2007 | Schmidt et al. | |
| 2007/0147189 A1 | 6/2007 | Schmidt et al. | |
| 2007/0148760 A1 | 6/2007 | Kiesel et al. | |
| 2007/0201025 A1 | 8/2007 | Greenwald | |
| 2008/0013092 A1 | 1/2008 | Maltezos et al. | |
| 2008/0013877 A1 | 1/2008 | Schmidt et al. | |
| 2008/0181827 A1 | 7/2008 | Bassler et al. | |
| 2008/0183418 A1 | 7/2008 | Bassler et al. | |
| 2008/0186483 A1 | 8/2008 | Kiesel et al. | |
| 2008/0186492 A1 | 8/2008 | Kiesel et al. | |
| 2008/0186494 A1 | 8/2008 | Kiesel et al. | |
| 2008/0186500 A1 | 8/2008 | Schmidt et al. | |
| 2008/0186503 A1 | 8/2008 | Kiesel et al. | |
| 2008/0186504 A1 | 8/2008 | Kiesel et al. | |
| 2008/0186508 A1 | 8/2008 | Kiesel et al. | |
| 2008/0187011 A1 | 8/2008 | Kiesel et al. | |
| 2009/0220189 A1 | 9/2009 | Kiesel et al. | |

FOREIGN PATENT DOCUMENTS

| | | |
|---|---|---|
| WO | WO 00/62050 A1 | 10/2000 |
| WO | WO 2005/108963 A1 | 11/2005 |
| WO | WO 2006/133360 A2 | 12/2006 |

OTHER PUBLICATIONS

Liang, X.J., Liu, A.Q., Zhang, X.M., Yap, P.H., Ayi, T.C., Yoon, H.S., "Refractive Index Measurement of Single Living Cell Using a Biophotonic Chip for Cancer Diagnosis Applications," 9th International Conference on Miniaturized Systems for Chemistry and Life Sciences, Oct. 9-13, 2005, 3 pages.

Agilent Technologies, "HPLC-Chip/MS Technology," 2 pages, printed Aug. 2, 2005 from www.chem.agilent.com.

Office communication in U.S. Appl. No. 11/702,325, mailed Aug. 15, 2008, 14 pages.

Amendment in U.S. Appl. No. 11/702,325, submitted Nov. 17, 2008, 38 pages.

Office communication in U.S. Appl. No. 11/702,325, mailed Feb. 10, 2009, 8 pages.

Amendment in U.S. Appl. No. 11/702,470, submitted Jul. 25, 2008, 21 pages.

Office communication in U.S. Appl. No. 11/702,470, mailed Oct. 31, 2008, 22 pages.

Amendment in U.S. Appl. No. 11/702,470, submitted Jan. 30, 2009, 22 pages.

Office communication in U.S. Appl. No. 11/702,363, mailed Sep. 4, 2008, 29 pages.

Amendment with Information Disclosure in U.S. Appl. No. 11/702,363, submitted Dec. 4, 2008, 34 pages.

Adams, M. L., Enzelberger, M., Quake, S., and Scherer, A., "Microfluidic integration on detector arrays for absorption and fluorescence micro-spectrometers," Sensors and Actuators, 2003, pp. 25-31.

Singh, K., Liu, C., Capjack, C., Rozmus, W., and Backhouse, C. J., "Analysis of cellular structure by light scattering measurements in a new cytometer design based on a liquid-core waveguide," IEE Proc.-Nanobiotechnol., vol. 151, No. 1, Feb. 2004, pp. 10-16.

Office communication in U.S. Appl. No. 11/702,470, mailed Apr. 25, 2008, 22 pages.
Notice of Allowance and Fee(s) Due in U.S. Appl. No. 11/702,250, mailed Jun. 18, 2008, 11 pages.
Communiction from European Patent Office, including extended European search report with European Search Report and Annex and European search report opinion for counterpart EPO Application No. 08151017.4, dated May 30, 2008, 6 pages.
Shapiro, H.M., Practical Flow Cytometry, Fourth Edition, Wiley-Liss, 2003, Table of Contents and pp. 49-59, 124-183, 191-197, and 364-366.
Hoffman, R.A., "Flow Cytometry: Instrumentation, Applications, Future Trends and Limitations", Springer Series on Fluorescence, vol. 6, 2008, pp. 307-342.
Notice of Allowance and Fee(s) Due in U.S. Appl. No. 11/702,470, mailed Apr. 24, 2009, 15 pages.
Notice of Allowance and Fee(s) Due in U.S. Appl. No. 11/702,363, mailed Mar. 23, 2009, 12 pages.
Response With Terminal Disclaimer in U.S. Appl. No. 11/702,325, submitted May 5, 2009, 5 pages.
Office communication in U.S. Appl. No. 11/702,325, mailed Aug. 28, 2009, 13 pages.
Amendment in U.S. Appl. No. 11/702,321, submitted May 8, 2009, 21 pages.
Notice of Allowance and Fee(s) Due in U.S. Appl. No. 11/702,321, mailed Aug. 11, 2009, 20 pages.
Amendment in U.S. Appl. No. 11/702,320, submitted May 7, 2009, 29 pages.
Office communication in U.S. Appl. No. 11/702,320, mailed Aug. 12, 2009, 9 pages.
Office communication in U.S. Appl. No. 11/702,329, mailed Aug. 24, 2009, 24 pages.
Submission to European Patent Office in counterpart EPO Application No. 08151017.4, dated Sep. 14, 2009, 17 pages.
Amendment in U.S. Appl. No. 11/702,320, submitted Nov. 3, 2009, 24 pages.
Amendment in U.S. Appl. No. 11/702,325, submitted Nov. 2, 2009, 25 pages.
Rule 312 Amendment in U.S. Appl. No. 11/702,321, submitted Oct. 27, 2009, 16 pages.
Amendment in U.S. Appl. No. 11/702,329, submitted Oct. 27, 2009, 23 pages.
Office communication in U.S. Appl. No. 11/702,320, mailed Feb. 24, 2010, 21 pages
Amendment with Terminal Disclaimer in U.S. Appl. No. 11/702,325, submitted Jan. 18, 2010, 20 pages.
Office communication in U.S. Appl. No. 11/702,325, mailed Feb. 4, 2010, 19 pages.
Office communication in U.S. Appl. No. 11/702,329, mailed Feb. 1, 2010, 15 pages.
Amendment in U.S. Appl. No. 11/702,329, submitted Mar. 8, 2010, 26 pages.
Amendment submitted on Mar. 17, 2010, from U.S. Appl. No. 11/702,325, 26 pages.
Office communication mailed Mar. 19, 2010, from U.S. Appl. No. 11/702,329, 2 pages.
Office communication mailed Mar. 24, 2010, from U.S. Appl. No. 11/702,325, 3 pages.
Amendment submitted on Apr. 8, 2010, from U.S. Appl. No. 11/702,320, 26 pages.
European Patent Office communication in EPO Patent Application No. 08171499.0-2319/2072006, mailed Feb. 5, 2010, 1 page.
An Office communication in U.S. Appl. No. 11/702,320, mailed Apr. 15, 2010, 3 pages.
An Office communication in U.S. Appl. No. 11/702,329, mailed May 17, 2010, 19 pages.
Amendment in EPO Application No. 08171499.0-2319/2072006, submitted Jun. 21, 2010, 32 pages.
Office communication in U.S. Appl. No. 11/702,325, mailed May 27, 2010, 23 pages.

* cited by examiner

FIG. 10
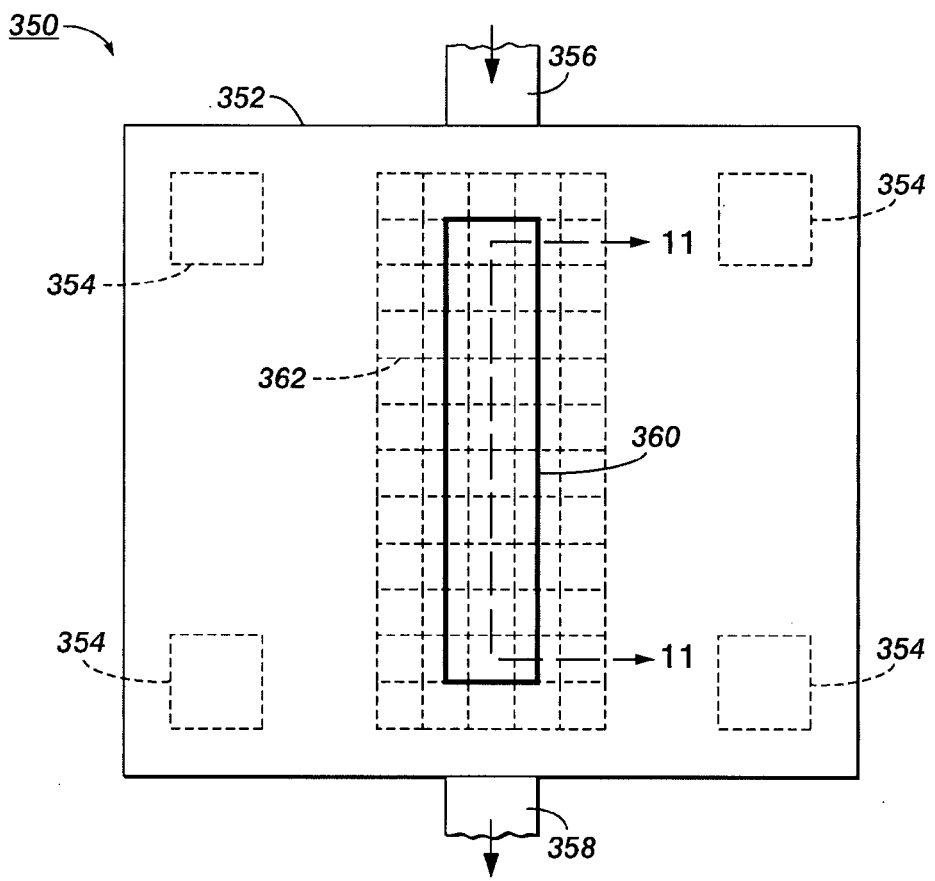
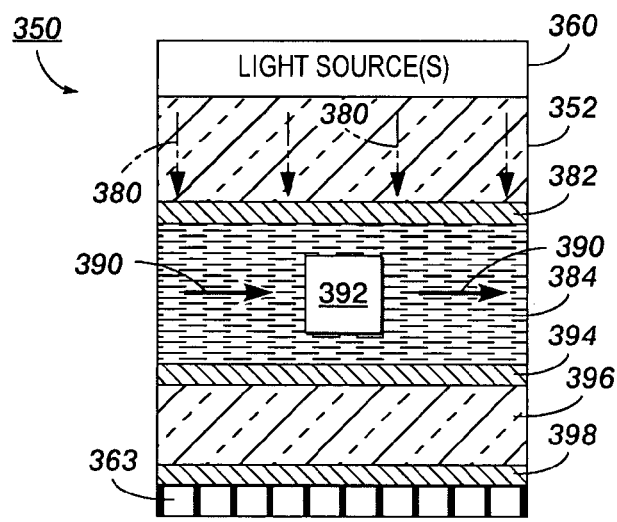
FIG. 11

FIG. 14
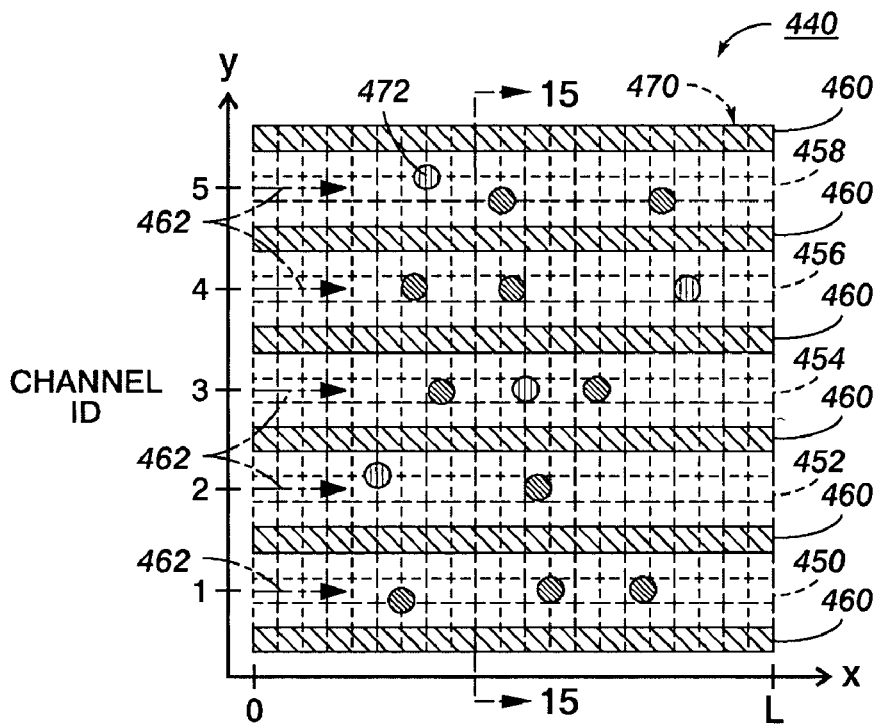
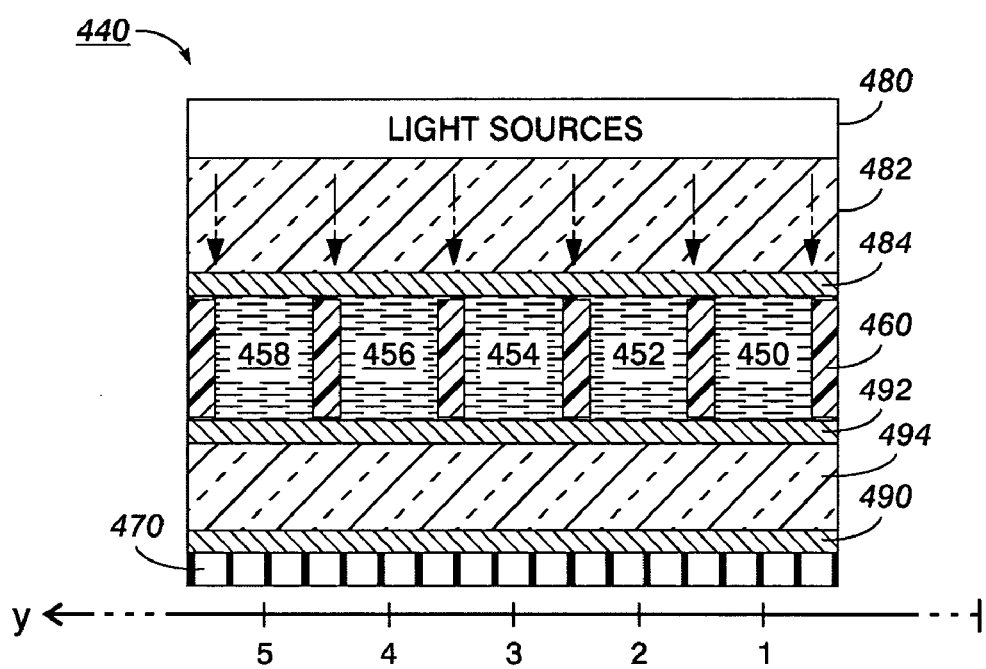
FIG. 15

FIG. 18
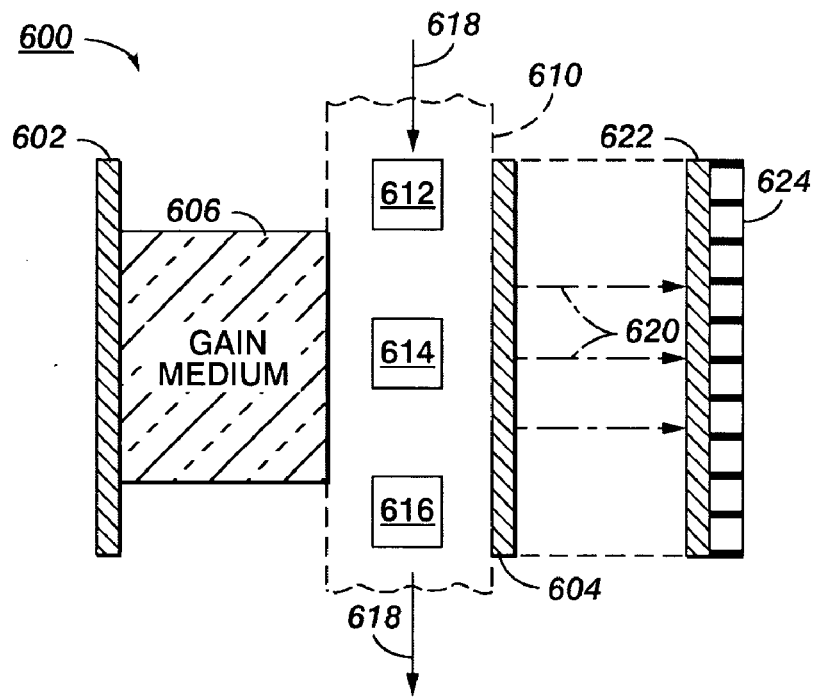
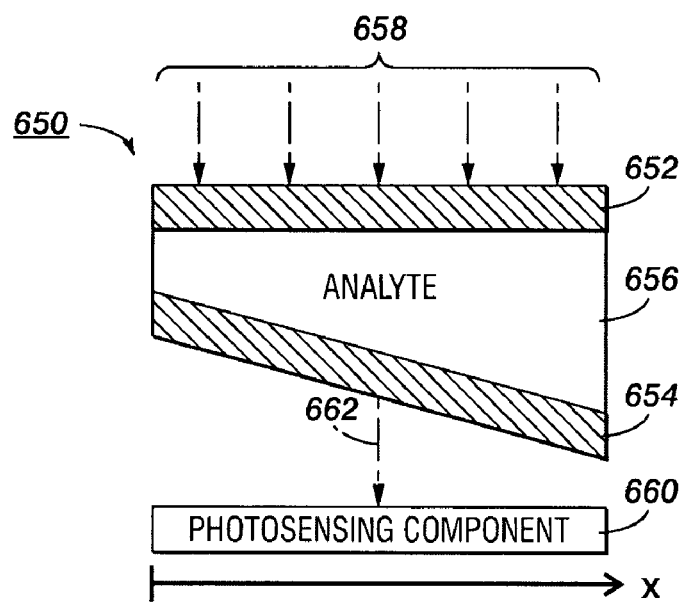
FIG. 19

DISTINGUISHING OBJECTS

This application is related to the following applications, each of which is hereby incorporated by reference in its entirety: "Chip-Size Wavelength Detector", U.S. patent application Ser. No. 10/922,870, now published as U.S. Patent Application Publication No. 2006/0039009; "Biosensor Using Microdisk Laser", U.S. patent application Ser. No. 10/930,758, now published as U.S. Patent Application Publication No. 2006/0046312; "Sensing Photon Energies Emanating From Channels or Moving Objects", U.S. patent application Ser. No. 11/315,992; "Photosensing Throughout Energy Range and in Subranges", U.S. patent application Ser. No. 11/316,438; "Obtaining Analyte Information", U.S. patent application Ser. No. 11/316,303; "Position-Based Response to Light", U.S. patent application Ser. No. 11/633,302; "Photosensing Optical Cavity Output Light", U.S. patent application Ser. No. 11/702,250; "Encoding Optical Cavity Output Light", U.S. patent application Ser. No. 11/702,363; "Obtaining Information From Optical Cavity Output Light", U.S. patent application Ser. No. 11/702,249; "Moving Analytes and Photosensors", U.S. patent application Ser. No. 11/702,470; "Implanting Optical Cavity Structures", U.S. patent application Ser. No. 11/702,329; "Containing Analyte In Optical Cavity Structures", U.S. patent application Ser. No. 11/702,325; "Tuning Optical Cavities", U.S. patent application Ser. No. 11/702,321; and "Tuning Optical Cavities", U.S. patent application Ser. No. 11/702,320.

BACKGROUND OF THE INVENTION

The present invention relates generally to techniques to distinguish objects, such as techniques that use information in output light from optical cavities to distinguish objects.

Liang X. J., Liu, A. Q., Zhang, X. M., Yap, P. H., Ayi, T. C., and Yoon, H. S., "Refractive Index Measurement of Single Living Cell Using a Biophotonic Chip for Cancer Diagnosis Applications," 9th International Conference on Miniaturized Systems for Chemistry and Life Sciences, Oct. 9-13, 2005, Boston, Mass., 2005, pp. 464-466 describe techniques that perform refractive index (RI) measurement of single living cells using a biophotonic chip for cancer diagnosis applications. Liang et al. describe a biophotonic chip that is formed by bonding a metal-coated glass slide with a PDMS slab molded using soft lithography technology. An analysis unit embedded in the chip to measure RI includes a laser diode with one surface opposite a gold-coated mirror, forming an external laser cavity. A microlens array in the chip improves beam quality, and living cells in a buffer are driven by electrokinetic force and delivered into an analysis region along microfluidic channels. A difference in RI between a cell and the buffer changes the effective cavity length so that laser emission varies, with a wavelength shift. The cell's effective RI can be computed by monitoring wavelength and power.

Table 1 from Liang shows a number of exemplary refractive indices relevant to cancerous cells.

TABLE 1

| Cell Type | Refractive Index |
| --- | --- |
| Culture medium | 1.350 |
| HeLa | 1.392 |
| PC12 | 1.395 |
| MDA-MB-231 | 1.399 |
| MCF-7 | 1.401 |
| Jurkat | 1.390 |

Liang et al. state that automatic measurement of RI of a living cell in real time offers low cost, high accuracy disease diagnosis.

It would be advantageous to have improved techniques for distinguishing objects, including improved techniques for using information in optical cavity output light to do so.

SUMMARY OF THE INVENTION

The invention provides various exemplary embodiments, including systems, methods, apparatus, and devices. In general, the embodiments involve distinguishing objects using information in optical cavity output light.

These and other features and advantages of exemplary embodiments of the invention are described below with reference to the accompanying drawings.

BRIEF DESCRIPTION OF THE DRAWINGS

FIG. 10 is a schematic top view of a device that can be used in a system implemented as in FIGS. 7 and 8.

FIG. 11 is a schematic cross section of the device of FIG. 10, taken along the line 11-11.

FIG. 14 is a schematic top view of a multiple channel device that can be used in a system implemented as in FIGS. 7 and 8.

FIG. 15 is a schematic cross section of the device of FIG. 14, taken along the line 15-15.

FIG. 18 is a schematic diagram of a setup that could be used in an implementation of a system as in FIGS. 7 and 8 in which analyte-containing objects such as biological cells pass through a laser cavity.

FIG. 19 is a schematic side view of a graded optical cavity that can contain analyte and could be used in a system as in FIGS. 7 and 8.

DETAILED DESCRIPTION

Figure 1:
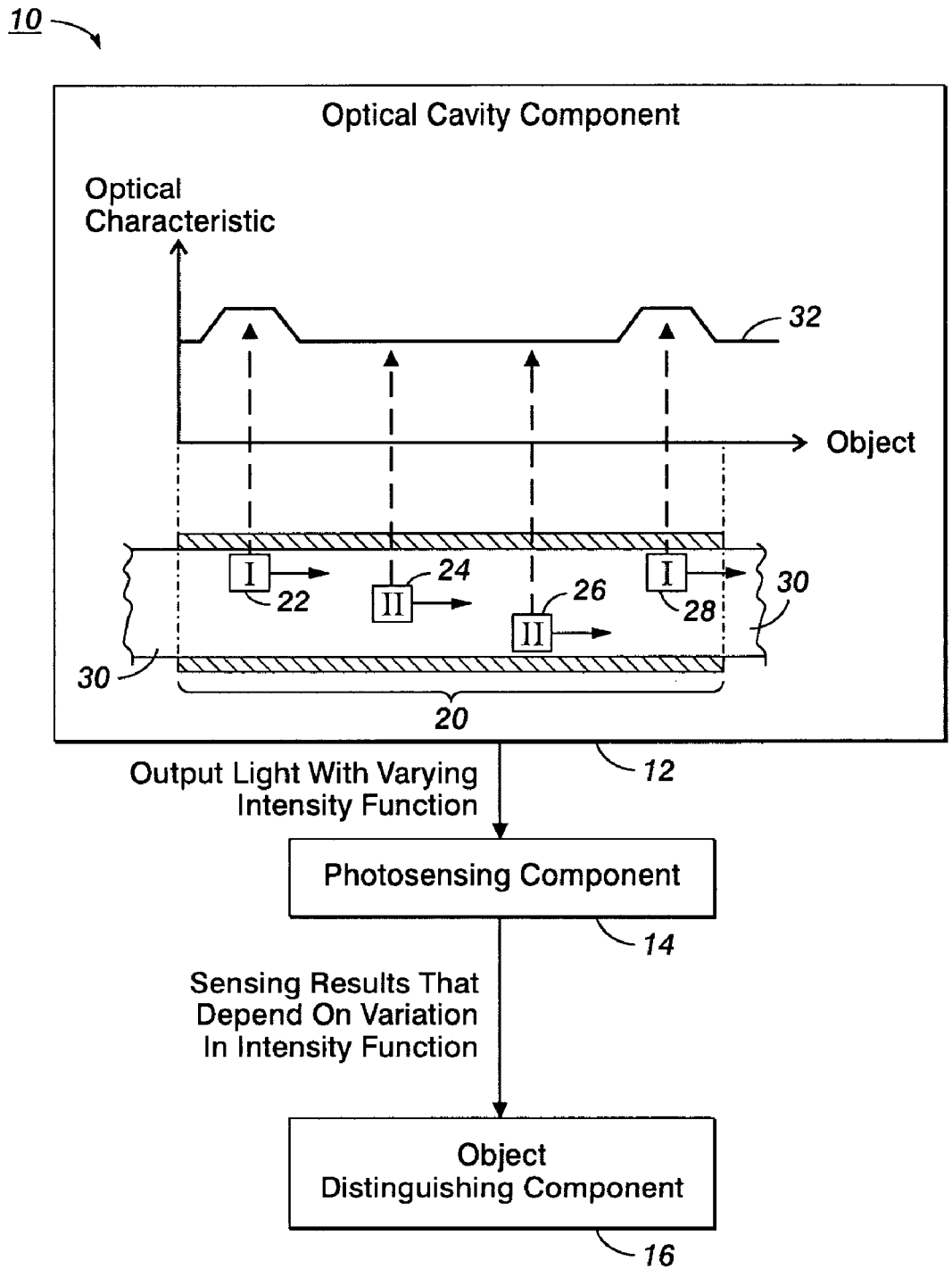
FIG. 1 is a schematic diagram of a system in which objects traveling through an optical cavity are distinguished based on information in output light from the cavity.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. The term "photon" refers herein to a quantum of light, and the term "photon energy" refers herein to the energy of a photon. Light can be described as having a "photon energy distribution", meaning the combination of photon energies that are included in the light; highly monochromatic light, for example, has a photon energy distribution with one peak energy value. A photon energy distribution can be specified in space and time: For example, a photon energy distribution can be specified as a function of position, such as on a surface, or as a function of time; a photon energy distribution that is "homogeneous" is substantially the same at all relevant positions, such as the positions of a surface, while a photon energy distribution that is "stable" is substantially the same at all relevant times.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, light emitting diodes (LEDs), superluminescent LEDs (SLEDs), resonant cavity LEDs, sources of broadband light that is spectrally filtered such as with a monochromator, and so forth. A "tunable light source" is a light source that provides light with a predominant photon energy that can be changed in response to a signal or operation of some kind.

The term "laser" is used herein to mean any region, element, component, or device in which transitions between energy levels can be stimulated to cause emission of coherent light, such as in the ultraviolet, visible, or infrared regions of the spectrum. A "laser structure" is any structure that includes one or more lasers. A "laser cavity" is a region of a laser in which transitions can be stimulated to cause emission.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where light changes direction in a way that can be illustrated as a vertex between an incoming ray and an outgoing ray, the change may be referred to as a "reflection"; similarly, to "reflect" light is to cause the light to change its direction of propagation approximately at a surface, referred to herein as a "reflection surface". Where light propagates at less than c, it may be useful to obtain an "optical distance" of propagation; for any segment of length d in which speed of propagation is constant $\in *C$, where $\in \leq 1$, optical distance $D(\in)=d/\in$. An optical distance may be referred to herein as an "optical thickness", such as where light is propagating through a thickness of material.

"Photon energy information" refers herein to information about photon energy, such as information about wavelength, frequency, wavelength shift, frequency shift, or a distribution of wavelengths or frequencies. "Absolute photon energy information" is information about a given photon energy value, such as a specific wavelength or frequency, while "relative photon energy information" is information that relates two photon energy values, whether measured concurrently or at different times.

To "photosense" is to sense photons, and to "photosense quantity" of photons is to obtain information indicating a quantity of the photons. Photons that are photosensed are sometimes referred to herein as "incident photons". A surface at which photosensing occurs is referred to herein as a "photosensitive surface".

A "photosensor" is used herein to refer generally to any element or combination of elements that senses photons, whether by photosensing quantity or any other information about the photons. A photosensor could, for example, provide an electrical signal or other signal that indicates results of sensing, such as a signal indicating quantity of incident photons; in general, signals from a photosensor that indicate results of sensing are referred to herein as "sensing results". If electrical sensing events occur in a photosensor in response to incident photons, the photosensor may integrate or otherwise accumulate the results of the electrical sensing events during a time period referred to herein as a "sensing period" or "sense period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described. A central wavelength or frequency or other value indicating a central photon energy of a range or subrange is sometimes referred to herein as a "central energy", and may be obtained in various ways, such as by finding an energy that has maximum intensity or that is another type of central value such as a mean or median of the distribution of light within the range or subrange.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry.

Circuitry can be described based on its operation or other characteristics. For example, circuitry that performs control operations is sometimes referred to herein as "control circuitry" and circuitry that performs processing operations is sometimes referred to herein as "processing circuitry".

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations of ICs described herein include features characterized as "cells" (or "elements") and "arrays", terms that are used with related meanings: An "array" is an arrangement of "cells" or "elements"; unless otherwise indicated by the context, such as for a biological cell, the words "cell" and "element" are used interchangeably herein to mean a cell or an element of an array. An array may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

An IC includes a "photosensor array" if the IC includes an array of cells, and at least some of the cells include respective photosensors. A cell that includes a photosensor may also include "cell circuitry", such as circuitry that makes connections with the photosensor, that transfers signals to or from the photosensor, or that performs any other operation other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application of an IC that includes a photosensor array, circuitry that "responds to" one or more photosensors can be any circuitry that, in operation, receives information from the photosensors about their photosensing results through an electrical connection. Circuitry that responds to a photosensor could be circuitry in the same cell as the photosensor, or it could be array circuitry, peripheral circuitry, or other external circuitry, or it could include any suitable combination of cell circuitry, array circuitry, peripheral circuitry, and other external circuitry. Circuitry that responds to a photosensor could employ any suitable technique to read out photosensing results, including, for example, CCD, CMOS, or photodetector array (PDA) techniques.

An IC is or includes a "position-sensitive detector" or "PSD" if it includes a substantially continuous photosensitive surface and it provides electrical signals indicating a position resulting from a pattern of incident light on the photosensitive surface. For example, the signals could be two currents whose normalized difference is proportional to a centroid of the incident light pattern.

FIG. 1 illustrates general features of system 10, an example of a system that can be implemented as described in greater detail below. As with other implementations described below, system 10 involves a combination of parts or components. As used herein, a "system" is a combination of two or more parts or components that can perform an operation together. A system may be characterized by its operation: for example, an "object distinguishing system" is a system that operates somehow to distinguish objects; a "processing system" is a system that performs data or signal processing; and so forth.

Within a system, components and parts may be referred to in a similar manner. One component of an analyte information system in which information is obtained about an analyte's optical characteristics, for example, can be a "detector component" or simply "detector", meaning a component that detects light; similarly, a "light source component" includes one or more light sources; an "optical component" performs an optical operation; a "photosensing component" performs a photosensing operation; a "light-transmissive component" or simply "transmission component" transmits light; a "light-reflective component" or simply "reflective component" reflects light; an "object distinguishing component" operates to distinguish objects; an "optical cavity component" includes an operable optical cavity; and other examples are defined further below. Other parts or components can be characterized by their structure.

System 10 includes optical cavity component 12, photosensing component 14, and object distinguishing component 16. Optical cavity component 12 includes optical cavity 20, through which objects can travel, carried by a medium such as a liquid, gas, aerosol, or other fluid.

The term "reflective optical cavity", or simply "optical cavity" or "cavity", refers herein to a light-transmissive region that is at least partially bounded by light-reflective components, with the light-reflective components and the light-transmissive region having characteristics such that a measurable portion of light within the light-transmissive region is reflected more than once across the light-transmissive region. An "optical cavity component" is a component that includes one or more optical cavities.

Within the broad category of optical cavities, there are various more specific types: For example, a laser cavity, mentioned above, is an example of an "emitting optical cavity" or simply "emitting cavity" that can operate as a source of emitted output light even when it is not receiving input light from an external light source, with the emitted light ordinarily resulting from a gain medium within the light-transmissive region; similarly, a "transmissive cavity" can operate, in response to input light from one or more external light sources at an entry surface, providing a transmitted portion of its output light at an exit surface different than the entry surface (a complementary, reflected portion may be provided at the entry surface); a "Fabry-Perot cavity" is a reflective optical cavity in which constructive interference (or positive reinforcement) occurs in one or more photon energy subranges while destructive interference occurs in others.

A Fabry-Perot cavity or other optical cavity that can operate to provide output light in one or more photon energy subranges while not providing output light with other photon energies may be described as having one or more "modes", each for a respective one of the output light energy subranges; if the cavity is a transmissive cavity, modes of its transmitted output light may be referred to as "transmission modes" and modes of its reflected output light may be referred to as "reflection modes". In the reflection spectrum, either the valley-like dips or the plateau-like reflection bands between the dips can be considered as "reflection modes". An emitting cavity can be described as "stimulated at" a mode by any operation that results in emission of output light in the mode's photon energy subrange. Similarly, a transmissive cavity can be described as "illuminated at" a mode by any operation that provides input light that results in transmission or reflection of output light in the mode's photon energy subrange.

In typical implementations of optical cavities, two light-reflective components have approximately parallel reflection surfaces and the light-transmissive region is sufficiently uniform that measurements would indicate many reflections of light within the light-transmissive region. Such cavities define a directional orientation as follows: Directions in which light could propagate and be reflected many times within the light-transmissive region are referred to herein as "reflection directions", and generally include a range of directions that are approximately perpendicular to both reflection surfaces. Directions that are approximately parallel to both reflection surfaces, on the other hand, are generally referred to herein as "lateral directions". In addition, the terms "in", "inward", or "internal" generally refer to positions, directions, and other items within or toward the light-transmissive region between the reflection surfaces, while "out", "outward", and "external" refer to positions, directions, and other items outside or away from the light-transmissive region. In general, it should be understood that the above directional orientation is arbitrary and only for ease of description, and that an optical cavity may have any appropriate orientation.

The above directional orientation does not in general apply to angle of incidence of input light. Transmissive cavities can typically operate in response to incident light that is not perpendicular to entry surfaces or reflection surfaces. Light incident on a transmissive cavity's entry surface at any angle is reflected multiple times within the cavity, producing transmission modes in accordance with the cavity's geometry. But transmission modes are affected by angle of incidence: Depending on the type of cavity and the angle of incidence, modes can be blue shifted or red shifted in comparison to perpendicular incidence; if all light enters a cavity at approximately the same angle, performance is affected only by the shifting of modes and modes are not also broadened, but performance is reduced if a cavity receives incident light distributed across a large angular range because transmission mode structure is then averaged over multiple angles.

The various exemplary implementations described below address problems that arise in distinguishing objects using information encoded in output light from optical cavities. The implementations are especially relevant to optical cavity output light that includes information about an optical characteristic of an object, which could in turn be an optical characteristic that results from an analyte within the object. One problem is the difficulty of obtaining high resolution information about optical characteristics rapidly and without bulky, expensive equipment; absorption spectroscopy, for example, typically requires a long interaction length between light and object to detect small absorption changes, so that large equipment is necessary. Another problem is that accurate information may be difficult to include in output light because of various types of noise that may be present in an optical system. Yet another problem is that techniques used to include information about one optical characteristic are usually not adapted for another characteristic, so that several different techniques must be used to include information about several optical characteristics in an optical cavity's output light.

The term "object" is used herein in the general sense of any distinguishable thing that can have optical characteristics such as refractive index and absorption. More generally, any energy shifting or loss mechanism associated with a distinguishable thing within the cavity affects transmitted and reflected wavelength and intensity, and is therefore a type of optical characteristic as used herein, including, for example, scattering and reflection.

Examples of objects that could occur in implementations as described herein include droplets, bubbles, small volumes of fluid, single molecules, agglomerated molecules, molecule clusters, biological cells, viruses, bacteria, proteins, DNA, microparticles, nanoparticles, and emulsions. A droplet or small volume of fluid may, for example, include atoms, molecules or other particles that affect refractive index, absorption, or other optical characteristics. An object "travels" or is caused "to travel" if the object moves through a succession of positions. For example, the object could be conveyed in a fluid, such as a liquid, gas, or aerosol, in which case the object may be referred to as being "carried by the fluid." More generally, an object travels through an optical cavity "in a medium" if the medium surrounds the object while the object is traveling through the cavity, whether or not the medium carries the object; in some implementations, an object could travel through a cavity in a medium even though the medium as a whole is not flowing. For example, the medium could be a porous material and a gas analyte could flow through it, such as by diffusion.

In addition to a medium's flow, an object could be caused to travel in the medium by any of various other factors, such as a difference in momentum, a difference in density, an electrical charge, a magnetic characteristic, a form of self-propulsion caused by chemical reaction or mechanical or biological operation, and so forth.

The term "path" is used herein to refer to a substantially continuous series of positions through which an object may travel. A path is "through a cavity" if an object following the path passes through part of the cavity. A photosensing component, such as an array or PSD, is "positioned along" or "along" a path through a cavity if the component is positioned near the cavity in such a way that, when an object following the path affects output light from the cavity, the photosensing component can obtain sensing results that include information about how the object is affecting the output light. An object following a path in such a case can be said to move "past the array".

An object is "present in", "positioned in", "contained in", or simply "in" an optical cavity when the object is in all or some part of the cavity's light-transmissive region. An optical cavity provides "object-affected output light" if the optical cavity's output light is different in some way when an object is present in the cavity than when the object is absent, with the difference being due to the object's optical characteristics.

In FIG. 1, for example, each of objects 22, 24, 26, and 28 is in optical cavity 20, and each is following a respective path through cavity 20, as indicated by an arrow for each object. Each object's path is in medium 30, which may or may not be flowing. As suggested by the numbers in the objects, the objects are of two or more types, with objects 22 and 28 illustratively of type I and with objects 24 and 26 illustratively of type II.

As shown by curve 32 in the graph above cavity 20, objects of each type affect an optical characteristic of cavity 20 differently from objects of other types, with objects of type I illustratively causing the optical characteristic to increase, while objects of type II do not. Because they affect the optical characteristic differently than medium 30 without objects, objects of type I may also be trackable objects if certain other constraints are met. As used herein, an operation "tracks" an object if it obtains information about position of the object; the term "trackable" therefore describes a type of objects that affect an optical characteristic of a cavity in such a way that, if constraints are met, information about position of each object of the type can be obtained. In contrast, a type of object is "non-trackable" if objects of the type do not have such an effect; an example of a non-trackable object would be an object that, in a medium, has no measurable effect on any optical characteristic of a cavity.

One way information about an object can be included in a cavity's output light can be used with a cavity that provides light in one or more modes, such as transmission modes or reflection modes. Each mode can have an "intensity function", meaning a function that represents output light intensity from the cavity (or from each mode) as a function, such as of photon energy or, in some implementations, of position. An intensity function, such as the intensity function of a mode, can be modified as a result of an object's presence to encode information about one or more optical characteristics of the object, providing object-affected output light that includes encoded information about the object's optical characteristics, such as about a value or a change in value of an optical characteristic, in which case the intensity function may be described as "object-encoded" herein.

While objects 22, 24, 26, and 28 travel through cavity 20, output light from cavity 20 could therefore have a "varying intensity function", meaning that an intensity function of the cavity, or of one of the modes in which it provides output light, varies in some way. It could vary during the time in which the objects are traveling through cavity 20, in which case it could be characterized as a "time varying intensity function". For example, if cavity 20 has a mode with an intensity peak, change in the peak, such as a change in one of its features, can occur as a function of time, depending for example on movement of objects 22 through 28. A varying intensity function could also vary as a function of lateral position, in which case it could be characterized as a "laterally varying intensity function". If the intensity function is, for example, an intensity-energy function, different lateral positions could have different intensity-energy functions; if an intensity-position function, different lateral positions could simply have different intensities.

A laterally varying intensity function can have any of a wide variety of shapes and features, but a shape that frequently arises in transmission modes is the "peak", a shape characterized by a maximum value from which a curve for the function slopes steeply downward. Peaks have various features, including "central value" meaning the value of the other parameter at which the peak's maximum occurs, such as "central energy" for an intensity-energy function; "maximum intensity" or simply "maximum" or "amplitude", meaning the intensity value at the peak's maximum, whether measured as an absolute intensity or relative to another feature, such as a nearby minimum value; "contrast", meaning a value indicating relationship between magnitudes of the peak's maximum intensity and of one or more nearby minima of the transmission intensity function; and "intermediate intensity width", meaning the width of the peak at an intensity somewhere between its maximum and nearby minima, such as a full width half maximum (FWHM). In general, information can be encoded in one of these features in various ways, including those described in co-pending U.S. patent application Ser. No. 11/702,363, entitled "Encoding Optical Cavity Output Light" and incorporated herein by reference in its entirety. Once encoded, such information can also be recovered in various ways, including those described in co-pending U.S. patent application Ser. No. 11/702,249, entitled "Obtaining Information From Optical Cavity Output Light" and incorporated herein by reference in its entirety.

As used herein, a variation in intensity function is "caused" by an object's travel through a cavity if the variation depends in some way on the object's position or movement as it travels. An object's travel causes "local variation" if a part of the cavity whose optical characteristic is affected by the object provides output light, sometimes referred to herein as "object's output light", that is somehow distinguishable from other parts of the output light based on position, such as a position at which it exits the cavity or the position at which it is incident on a photosensitive surface, with or without filtering or other optical operations between cavity and photosensitive surface. Variation of an intensity function that is not a local variation can be referred to as "non-local variation"; an example would be a variation that affects all output light from the cavity as a function of time but not of position, as could occur where output light is highly collimated, such as from a laser cavity.

Photosensing component 14 photosenses output light along optical cavity 20. This can be done, for example, with photosensing elements in one or more arrays or with one or more PSDs. The sensing results depend on the varying intensity function.

Object distinguishing component 16 uses the sensing results to track a set of one or more objects of trackable types, and therefore distinguishes the objects, i.e. from their environment or background. Component 16 can also distinguish at least one of the tracked objects in the set from one or more objects of other types. As used herein, an operation "distinguishes" objects if the operation locates, selects, sorts, counts, or otherwise identifies the objects or controls or directs the objects according to type or separates the objects or otherwise treats the objects differently in some way; for example, component 16 could distinguish each object of type I from objects of type II, such as by identifying tracked objects of the two types differently or causing tracked objects of the two types to follow different paths or to be separated or to undergo different operations in some other way after they exit from cavity 20, whether or not they remain within system 10.

The general features in FIG. 1 could be implemented in many ways, as exemplified by the various implementations described below. In particular, the exemplary implementations below include examples of various ways in which output light from a cavity could be object-encoded to provide information about optical characteristics of objects traveling through the cavity. The exemplary implementations also include various examples of optical cavity operation that perform object-encoding of various kinds, and further examples of positioning an object in an optical cavity and of encoding information in output light are described in co-pending U.S. patent application Ser. No. 11/702,363, entitled "Encoding Optical Cavity Output Light" and incorporated herein by reference in its entirety.

Many different types of mirrors and other light-reflective components could be used in an optical cavity device, some of which are described below. Similarly, light-transmissive regions of optical cavities could be implemented in many different ways, some of which are described below.

Photosensing component 14 could be implemented in many different ways, such as with a photosensing IC, as described in co-pending U.S. patent application Ser. No. 11/702,250, entitled "Photosensing Optical Cavity Output Light" and incorporated by reference herein in its entirety.

Object distinguishing component 16 could also be implemented in many different ways to perform a wide variety of different object distinguishing operations. Some specific examples are described below, including the possibility of distinguishing cancerous from non-cancerous cells, but many other object distinguishing operations could be performed, including a wide variety of operations that distinguish objects from their environment or background or distinguish between objects of different biological or chemical types.

Figure 2:
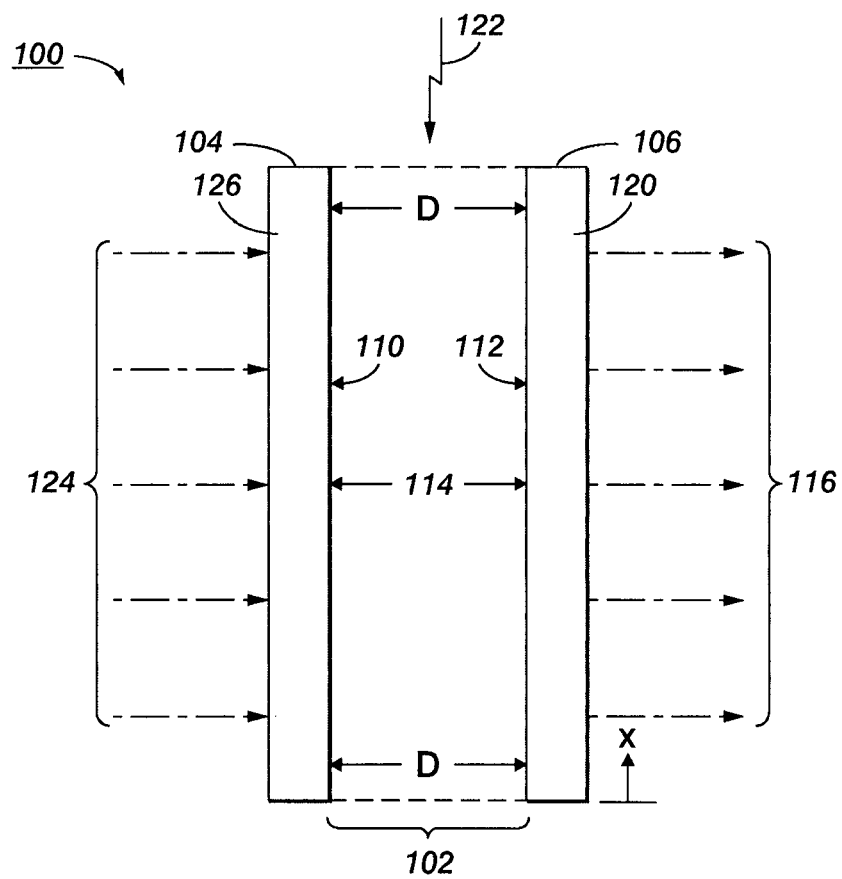
FIG. 2 is a schematic side view of a homogeneous optical cavity that could be used in the system of FIG. 1.

FIG. 2 illustrates optical cavity 100, an example of a "homogeneous optical cavity", meaning a cavity whose light-transmissive region includes an extended part with substantially constant optical distance D between its reflection surfaces, sometimes referred to as its "homogeneous region". The homogeneous region of cavity 100 illustratively includes substantially all of light-transmissive region 102 where it is between and partially bounded by light-reflective components 104 and 106, though partially and completely bounded homogeneous regions with various other shapes and arrangements are possible.

Inward-facing surfaces 110 and 112 of components 104 and 106, respectively, can be implemented, for example, as mirrors or other reflective components that closely approximate the reflection surfaces of cavity 100. The characteristics of components 104 and 106 and of any material or structure within region 102 are such that a measurement would indicate that at least a portion of light within region 102 is reflected more than once. A reflection direction in which light can be repeatedly reflected between the reflection surfaces is represented by bidirectional ray 114, while one of the possible lateral directions in an x-y plane approximately perpendicular to ray 114 is illustrated by an x-axis at the lower right.

FIG. 2 also illustrates two ways in which homogeneous optical cavities can operate to provide output light, represented schematically by arrows 116. In both operations, output light can be provided at an exit surface, illustratively outward-facing surface 120 of component 106, which may or may not be approximately parallel to the reflection surfaces.

In the first operation, optical cavity 100 operates as an emitting cavity, such as a laser cavity. Typically, an emitting cavity operates in response to stimulation of some type, represented schematically in FIG. 2 by stimulation arrow 122. Stimulation arrow 122 could, for example, represent electrical or optical stimulation.

In the second operation, optical cavity 100 operates as a transmissive cavity, such as a Fabry-Perot interferometer. A transmissive cavity operates in response to input light from one or more external light sources, represented in FIG. 2 by illumination arrows 124. Input light can be received at an entry surface, illustratively outward-facing surface 126 of component 104, which also may or may not be approximately parallel to the reflection surfaces. As noted above, a reflected portion of output light can be provided at the entry surface, as described in greater detail below.

Figure 3:
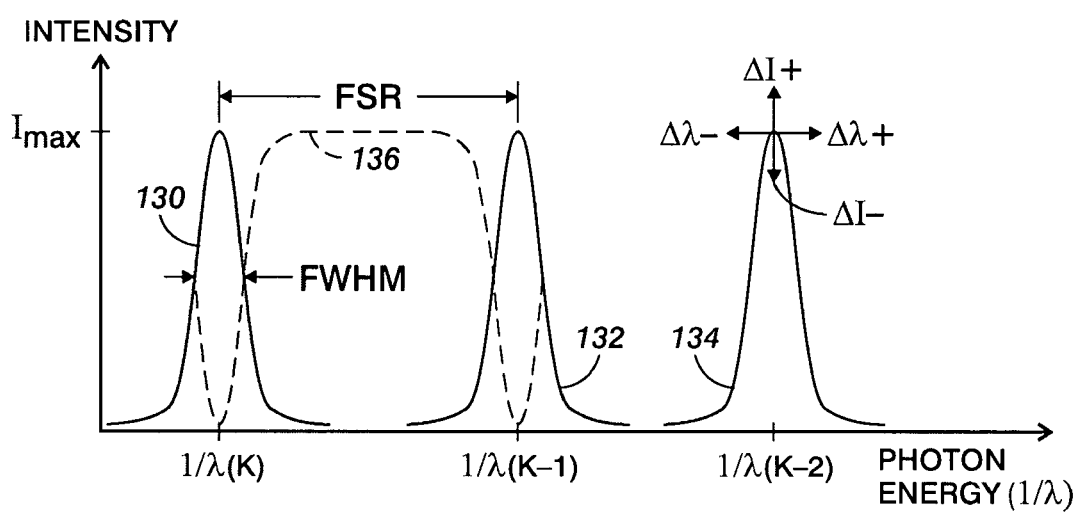
FIG. 3 is a graph showing intensity-energy curves for transmission and reflection from a cavity as in FIG. 2 when operated as a Fabry-Perot cavity, showing ways in which information can be included in transmission mode peaks.

FIG. 3 is an intensity-energy graph or "output spectrum" for optical cavity 100 when operated as a Fabry-Perot cavity such as an interferometer. Since photon energy is inversely proportional to wavelength, wavelength increases as one moves leftward along the horizontal axis, while the inverse of the wavelength ($1/\lambda$) increases as one moves rightward, as suggested by the labeling of points on the horizontal axis; it follows that energy and frequency would also increase to the right.

The graph in FIG. 3 includes a solid-line curve with peaks 130, 132, and 134, each of which is an "intensity-energy peak" or simply "intensity peak" that results from a respective transmission mode of cavity 100, illustratively the Kth, (K-1)th, and (K-2)th modes, and has an amplitude Imax, which could result from broadband illumination in the photon energy subranges of all the modes shown; such a curve is sometimes referred to herein as a "transmission spectrum". FIG. 3 also includes part of dashed-line curve 136 that is the complement of the transmission spectrum, i.e. the intensity-energy curve for light that is reflected rather than transmitted by optical cavity 100; such a curve is sometimes referred to herein as a "reflection spectrum" and its reflection modes are broad and separated by narrow valleys rather than being narrow peaks separated by broad valleys like the transmission modes. The term "output modes" is sometimes used herein as a generic term that encompasses transmission modes and reflection modes.

The maxima of intensity-energy peaks 130, 132, and 134 (and the complementary minima between reflection bands) are spaced apart as a function of photon energy (illustratively wavelength), and the difference between the central energy of adjacent transmission mode peaks is referred to as "free spectral range" or "FSR". FSR can be treated as the bandwidth over which adjacent intensity-energy peaks do not overlap, while the full width half maximum (FWHM) of the peaks can be treated as the minimum resolvable bandwidth. FSR, FWHM, and their ratio are all sometimes treated as figures of merit in designing a Fabry-Perot cavity.

The wavelength $\lambda$ of each intensity-energy peak can be obtained from the equation $\lambda(k)=2nD/k$, where n is the refractive index of the cavity and k is a non-zero integer. Therefore, if refractive index of the cavity changes, $\lambda(k)$ also changes for a given value of k, so that if a peak's central energy changes, as indicated by $\Delta\lambda+$ and $\Delta\lambda-$ for peak 134, the change provides information about refractive index change. Similarly, the intensity of the peaks depends on absorption in the cavity, so that if the intensity of a peak departs from Imax, as indicated by $\Delta I+$ and $\Delta I-$ for peak 134, the change provides information about absorption change.

Figure 4:
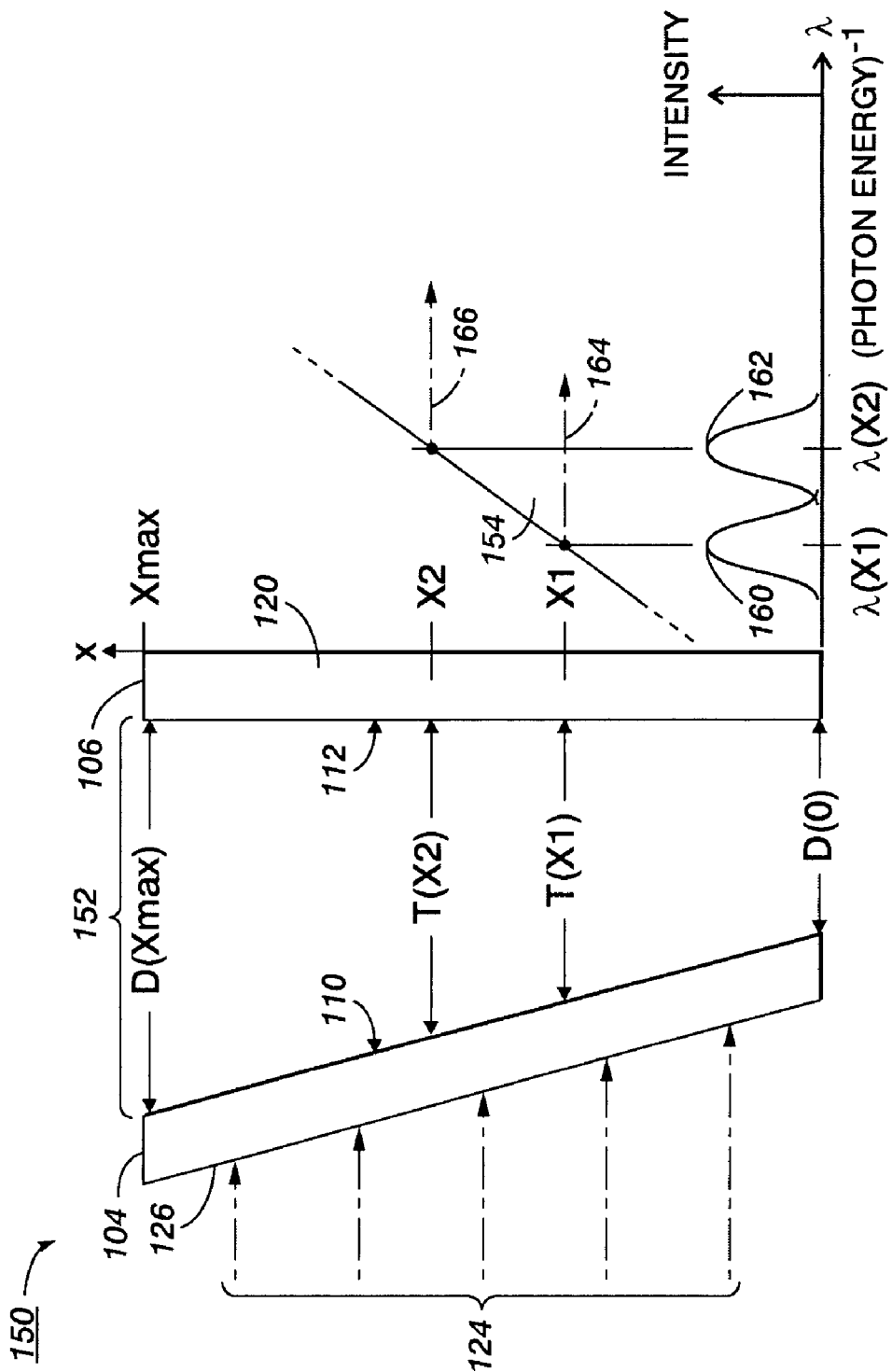
FIG. 4 is a schematic side view of a graded optical cavity that is an example of an inhomogeneous optical cavity that could be used in the system of FIG. 1.

FIG. 4 illustrates graded optical cavity 150, an example of an "inhomogeneous optical cavity", meaning a cavity that does not meet the above definition of a homogeneous optical cavity. Because of the similarities between cavities 150 and 100, parts and components of cavity 150 that are substantially the same as those in FIG. 2 are labeled with the same reference numbers. In cavity 150, however, region 152 is not homogeneous, but rather has "laterally varying optical distance" between reflective surfaces, meaning that the optical distance varies in one or more lateral directions; in the illustrated example, the optical distance illustratively increases linearly from D(0) at one end of cavity 150 (x=0) to D(Xmax) at the opposite end (x=Xmax), but optical distance between reflective surfaces in an inhomogeneous optical cavity could vary laterally in any appropriate way, and need not vary monotonically, linearly, or with any other type of uniformity.

Because of its linearly varying optical distance or thickness, cavity 150 can operate as a linearly variable optical filter (LVF), a type of transmissive cavity. This capability is illustrated by the function T(x), a "laterally varying energy output function", meaning that photon energies of output light depend on lateral position; in this case, the function relates output photon energy (in response to input light represented by illumination arrows 124) to lateral position on exit surface 120. For an LVF, the simple relationship $\lambda(x)=T(x)=d'x+\lambda(0)$ can hold, where d' is a constant that depends on gradient of optical thickness and can be graphically represented by the constant slope $(\lambda(X2)-\lambda(X1))/(X2-X1))$ of position-wavelength graph 154 at right in FIG. 4.

In general, the characteristics of output light at each position on surface 120 can be a function of parameters other than optical thickness, including, for example, photon energy and incident direction of input light 124 received at counterpart positions on surface 126. In particular, the output light may depend on whether the input light is narrow band, broad band, or multi-modal, as can result from a set of transmission or reflection modes. Narrow band or multi-modal illumination of an LVF, for example, can produce one or several output light spots, respectively.

The graphs at right in FIG. 4 also illustrate intensity-energy peaks 160 and 162 that would result if cavity 150 were illuminated by narrow band input light with central energy of $\lambda(X1)$ and $\lambda(X2)$, respectively, and, in response, operated as an LVF as described above. At position X1, for example, T(X1) results in transmission of output light represented by arrow 164, within a photon energy subrange characterized by central energy $\lambda(X1)$; at position X2, T(X2) results in transmission of output light represented by arrow 166, within a photon energy subrange characterized by central energy $\lambda(X2)$; for the illustrated laterally varying energy output function, if $X1 \neq X2$ and the difference between X2 and X1 is sufficient, then $T(X1) \neq T(X2)$, and $\lambda(X1) \neq \lambda(X2)$. On the other hand, for relatively small regions of output surface 120, cavity 150 might in some cases operate locally as a homogeneous cavity with transmission modes as illustrated in FIG. 3. It follows that parameters applicable to transmission modes are sometimes also useful for intensity-energy peaks from inhomogeneous cavities; in particular, information about changes in refractive index and absorption can sometimes be provided through changes in intensity-energy peaks in ways shown in FIG. 3.

Various techniques can be used to operate optical cavities to produce "laterally varying photon energy distributions" or simply "laterally varying energy distributions", meaning distributions in which photon energy of light varies as a function of lateral position. Such distributions can be produced, for example, with inhomogeneous optical cavities having laterally varying optical thicknesses and, even with homogeneous optical cavities, with angled illumination from a point light source rather than perpendicular illumination; several possible techniques are described in co-pending U.S. patent application Ser. No. 11/316,438, entitled "Photosensing Throughout Energy Range and in Subranges" and incorporated herein by reference in its entirety.

More generally, an inhomogeneous optical cavity can have any appropriate laterally varying energy output function, including functions that are nonlinear or nonuniform in other ways. Some of the below-described implementations, for example, involve functions that are affected by presence of an analyte in an optical cavity. As with homogeneous cavities, an inhomogeneous cavity's light-transmissive region can be completely between and partially bounded by light-reflective components as in FIG. 4, but partially and completely bounded light-transmissive regions with various other shapes and arrangements are possible.

Figure 5:
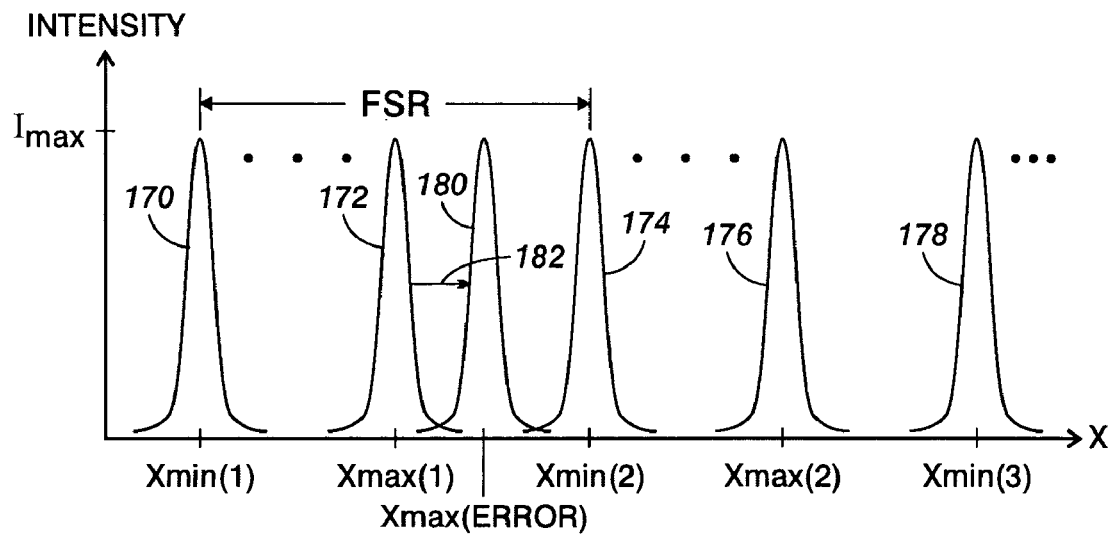
FIG. 5 is a graph showing an intensity-position function of a cavity as in FIG. 4, showing both spectral and harmonic relationships between peaks.

FIG. 5 is an intensity-position graph for optical cavity 150 when operated as a Fabry-Perot cavity such as an interferometer. FIG. 5 is similar to FIG. 3, and the peaks illustratively have maximum amplitude Imax as in FIG. 3 and their central energies and amplitudes (and FWHMs) could be affected as shown for peak 134 in FIG. 3; but the x-axis in FIG. 5 represents position in the x-direction in FIG. 4 rather than photon energy.

In the example shown in FIG. 5, cavity 150 is illuminated at P ($P \geq 2$) photon energies ranging from $\lambda$min to $\lambda$max, resulting in a series of output modes (illustratively transmission modes) for each photon energy $\lambda(p)$ of illumination at those positions on the x-axis where the condition $\lambda(p)=2n*D(x)/k$ is satisfied for integer values of k. The first transmission mode shown for $\lambda$min is peak 170 at x=Xmin(1) and for $\lambda$max is peak 172 at x=Xmax(1). The second transmission mode shown for $\lambda$min is peak 174 at x=Xmin(2) and for $\lambda$max is peak 176 at x=Xmax(2). The third transmission mode shown for λmin is peak 178 at x=Xmin(3), and so forth.

In the example of FIG. 5, transmission modes are sufficiently separated along the x-axis to prevent interference between adjacent transmission modes. As can be seen, Xmin (2) is sufficiently greater than Xmax(1) that peaks 172 and 174 do not interfere, and Xmin(3) is similarly sufficiently greater than Xmax(2) that peaks 176 and 178 do not interfere. If instead the first transmission mode of λmax were peak 180 due to an increase from Xmax(1) to Xmax(error), as indicated by arrow 182, interference between peaks 180 and 174 would begin to occur; as the first transmission mode of λmax increased further, loss of information would occur due to ambiguity between peak 180 and peak 174. Problems of this type can be avoided by coordination of photon energy range with cavity parameters; for example, cavity thickness D can be sufficiently small that only one output mode occurs over the range from λmin to λmax. The free spatial range (FSR) between the modes in a particular wavelength range can also be increased by reducing the tilt of the inhomogeneous (graded) cavity.

Figure 6:
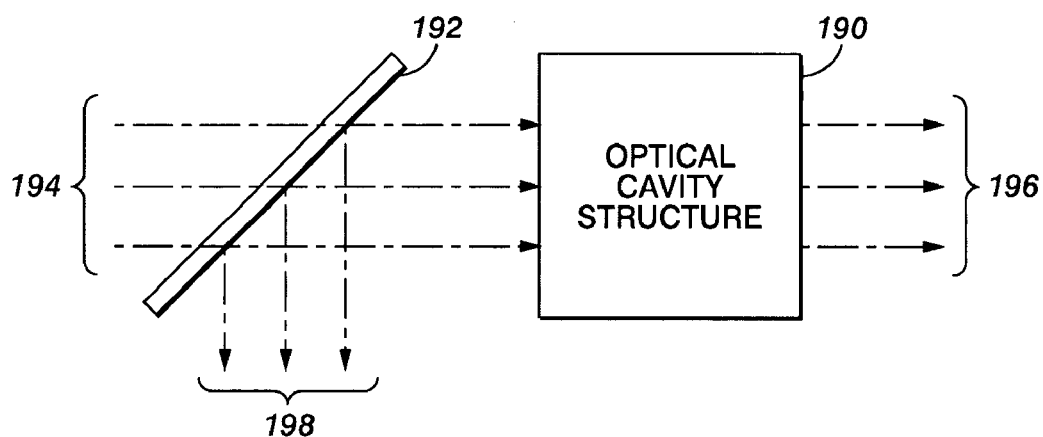
FIG. 6 is a schematic diagram of a setup in which an optical cavity as in FIG. 2 or 4 could operate to provide output light with reflection modes.

FIG. 6 shows a setup in which optical cavity structure 190 receives input light represented by arrows 192 through beam splitter 194. Optical cavity structure 190 can include a transmissive cavity implemented as in any of the ways described in relation to FIGS. 2-5 or in any other suitable way. In response to the input light, the cavity provides a transmitted portion of output light represented by arrows 196 and a reflected portion of output light represented by arrows 198. The use of beam splitter 194 is merely illustrative of ways in which input light and reflected light could be separated; for example, input light could be incident upon an entry surface at a sufficiently large angle from the normal that reflected light is separated from input light, though the non-perpendicular angle of incidence reduces performance of the optical cavity.

As suggested above in relation to FIG. 3, refractive index changes in the optical cavity will cause the same shift in both transmitted and reflected modes, while absorption in the optical cavity will similarly cause decreased amplitude and contrast and increased FWHM in both portions, with the effect of absorption typically varying as a function of photon energy; a curve showing absorption as a function of photon energy is sometimes referred to herein as an "absorption spectrum".

Figure 7:
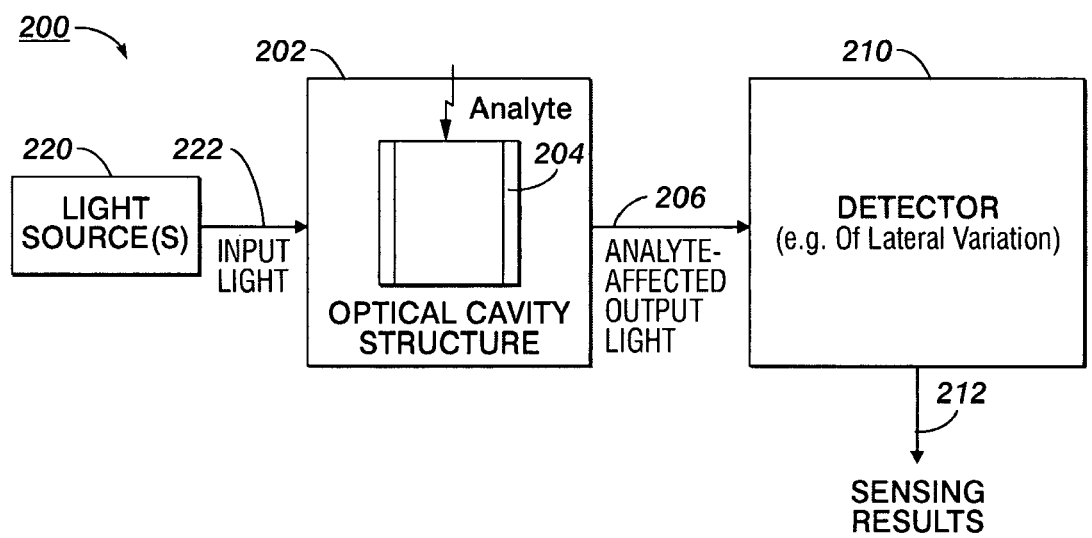
FIG. 7 is a schematic diagram of an implementation of the system of FIG. 1.

FIG. 7 shows system 200, an exemplary implementation of system 100 in FIG. 1. System 200 includes optical cavity structure 202, a structure that can include one or more optical cavities with features described above. In system 200, at least one of the optical cavities in structure 202, represented schematically by cavity 204, can contain an analyte, illustratively being provided to cavity 204. The presence of analyte in cavity 204 affects the output light provided by structure 202, and the analyte-affected output light, represented by arrow 206, can then be photosensed within detector 210. For example, detector 210 may include a photosensing component with one or more photosensitive surfaces at which lateral variation of light is detected, such as after the light passes through an LVF. The sensing results from detector 210 can be provided to other components within system 200 or to external components, as represented by arrow 212.

Detector 210 could be implemented in many different ways, such as with a photosensing IC, as described in co-pending U.S. patent application Ser. No. 11/702,250, entitled "Photosensing Optical Cavity Output Light" and incorporated by reference herein in its entirety. The implementation in FIG. 7 might, however, alternatively be implemented with photosensing components that do not include photosensing ICs, such as with one or more discrete photodiodes.

Although cavity 204 can be any suitable type of homogeneous or inhomogeneous optical cavity, including an emitting cavity or a transmissive cavity, FIG. 7 illustratively shows one or more light sources 220 that can be included within system 200 to illuminate one or more optical cavities. As represented by arrow 222, structure 202 receives input light from light sources 220. If optical cavity 204 is illuminated as shown, the analyte-affected output light represented by arrow 206 could include one or both of transmitted and reflected light.

Figure 8:
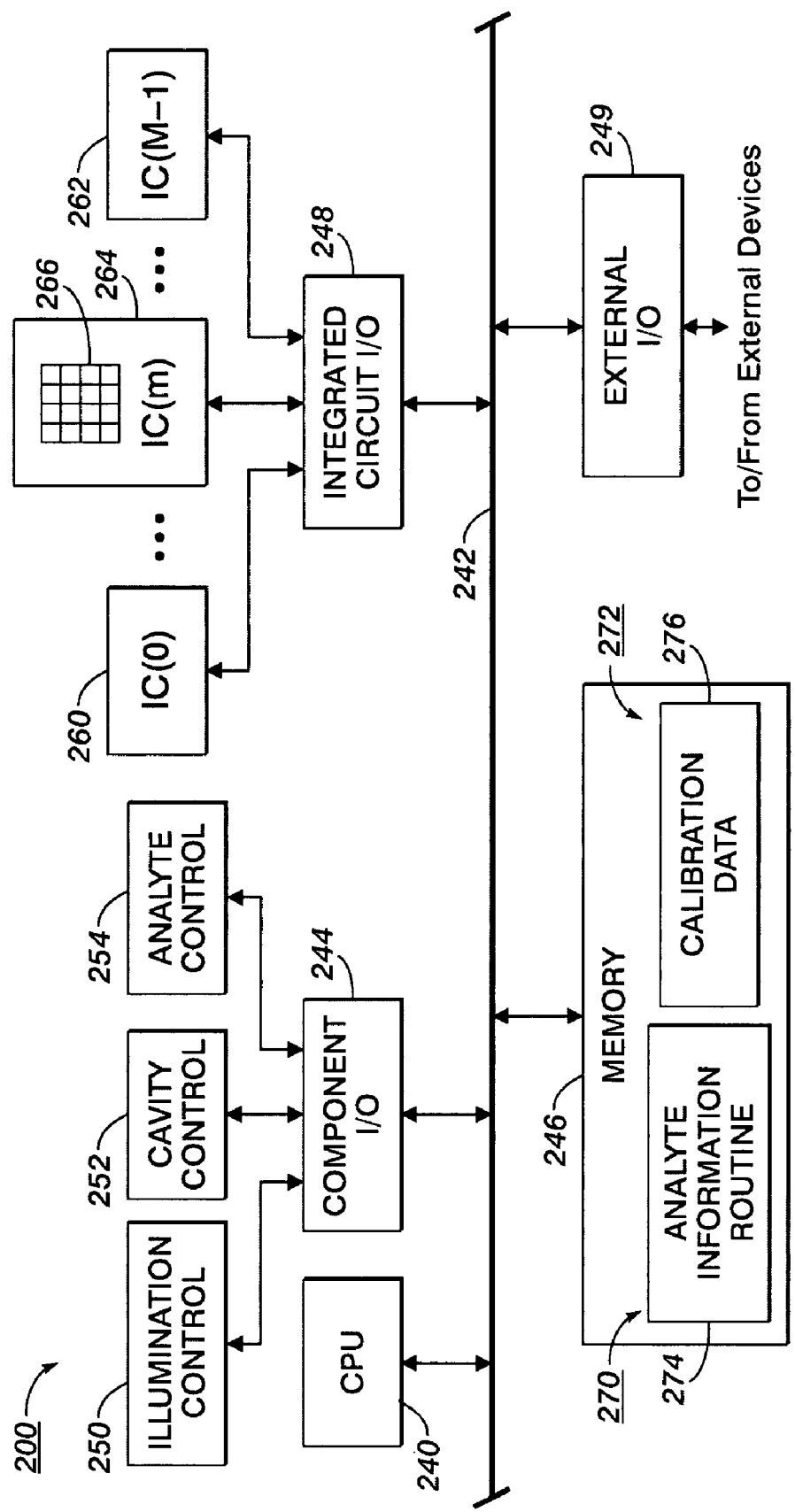
FIG. 8 is a schematic circuit diagram of a system implemented as in FIG. 7.

FIG. 8 illustrates electrical components that can be used in implementing system 200 as in FIG. 7. System 200 illustratively includes central processing unit (CPU) 240 connected to various components through bus 242, but a wide variety of other architectures could be employed, including any appropriate combination of hardware and software, as well as specialized hardware components such as application specific integrated circuits (ASICs) for one or more of the illustrated components or in place of a software component executed by CPU 240.

System 200 also includes component input/output (I/O) component 244, memory 246, integrated circuit input/output (IC I/O) 248, and external I/O 249, all connected to bus 242. System 200 can include various other components (not shown) connected to bus 242. In addition to connections through external I/O 249 by which signals can be provided to and received from external devices, bus 242 can also be connected directly to components outside of system 200.

Component I/O 244 permits CPU 240 to communicate with certain components of system 200, illustratively including illumination control 250, cavity control 252, and analyte control 254. For interactive applications, component I/O 244 could also be connected to a suitable user interface, such as a monitor and keyboard (not shown). In the exemplary implementation in FIG. 7, illumination control 250 can include light sources 220 (FIG. 7) and circuitry for controlling them; cavity control 252 can include electrodes or other components that can be operated to control cavity 204 and other cavities and can also include circuitry connected to those components; and analyte control 254 can similarly include fluidic devices or other components that can operate to transfer analyte into, through, or out of cavity 204 or other cavities or to produce relative movement between analyte and an array or a cavity, and can also include circuitry connected to those devices and components.

In the illustrated implementation of system 200, IC I/O 248 is a similar I/O component that permits CPU 240 to communicate with one or more ICs, such as in detector 210 in FIG. 5. M ICs are illustrated by a series from IC(0) 260 to IC(M−1) 262, including IC(m) 264 with a photosensor array 266.

Memory 246 illustratively includes program memory 270 and data memory 272, although instructions for execution by CPU 240 and data access during execution of instructions could be provided in any suitable way, including through external devices or components. The routines stored in program memory 270 illustratively include analyte information routine 274. In addition, program memory 270 could store various additional routines and also subroutines (not shown) that CPU 240 could call in executing routine 274. Similarly, the data in data memory 272 illustratively include calibration data 276, but could include various additional items of data and data structures accessed by CPU 240.

In executing routine 274, CPU 240 can provide signals to cavity control 252 and to analyte control 254 so that an analyte is present in cavity 204, for example, with the analyte having optical characteristics that affect output light from cavity 204. CPU 240 can also provide signals to illumination control 250 so that cavity 204 is appropriately illuminated to provide analyte-affected output light. CPU 240 can also provide signals to each of ICs 260 through 262 to obtain sensing results that include information about the analyte in cavity 204. In an implementation with a position-sensitive detector (PSD), CPU 240 could instead provide whatever signals are necessary to obtain photosensed quantities from the PSD; for example, CPU 240 could control circuitry to connect output currents from the PSD to a differential amplifier.

Figure 9:
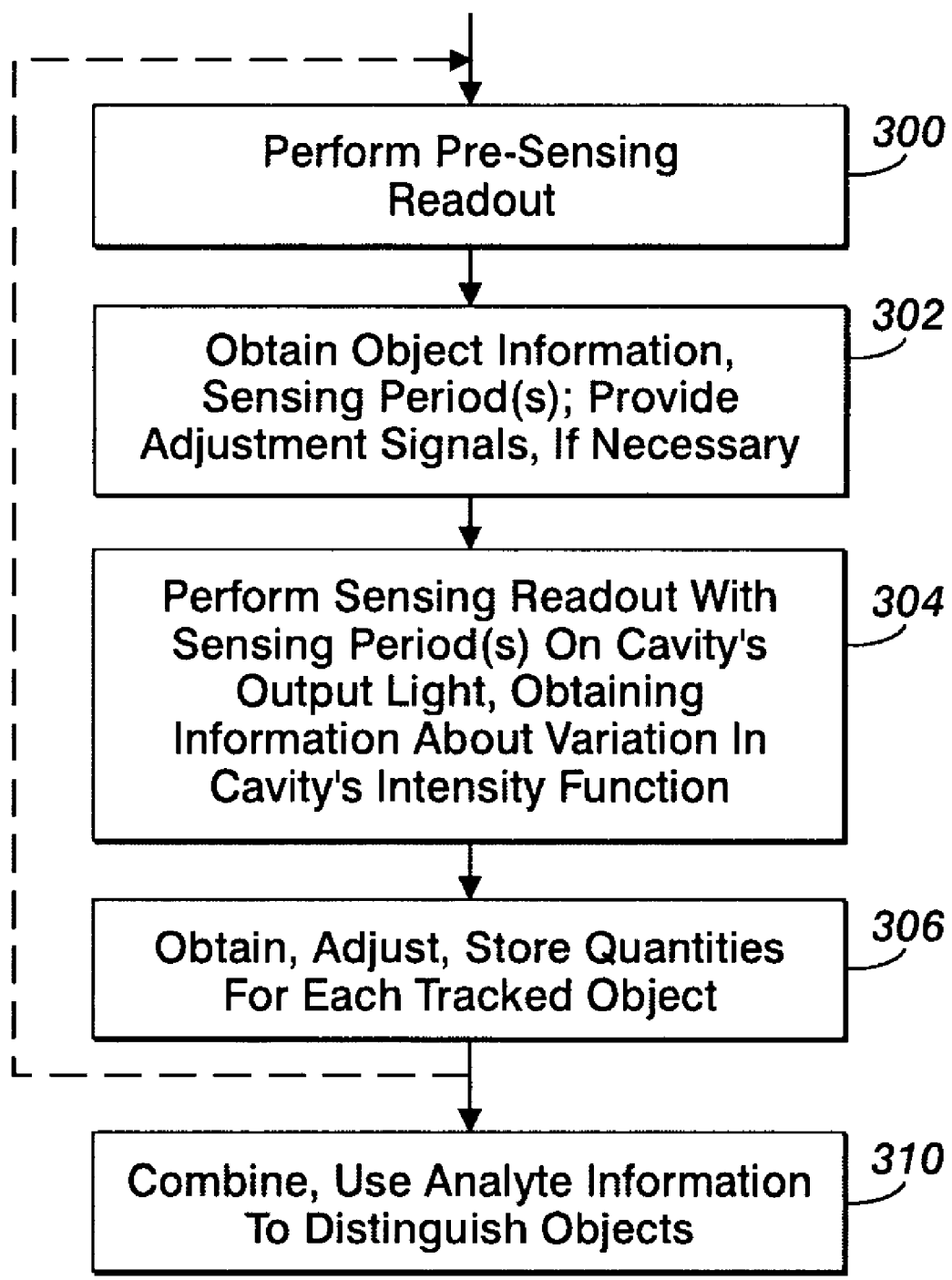
FIG. 9 is a flow diagram showing operations of the analyte information routine in FIG. 8.

FIG. 9 illustrates one example of how analyte information routine 274 could be implemented in a system like system 200 in FIGS. 7 and 8. The routine in FIG. 9 could be implemented with a variety of object distinguishing operations, such as locating, counting, sorting, selecting, directing, separating, and so forth. Therefore, in performing the routine in FIG. 9, CPU 240 operates as an object distinguishing component as described above.

The routine in FIG. 9 follows a general strategy of performing a series of readout operations, after which information is combined and used to distinguish objects. It would also be possible to use the information from each readout operation immediately or to use information both immediately after each readout operation and also after a series of readout operations.

When CPU 240 executes the operation in box 300, it performs a pre-sensing readout. The purpose is to obtain information necessary to later perform a sensing readout. The information could be obtained in the ways described in co-pending U.S. patent application Ser. No. 11/315,992, entitled "Sensing Photons from Objects in Channels" and incorporated herein by reference in its entirety.

Using the information from box 300, CPU 240 could obtain information about each object and determine an appropriate sensing period for each object, in the operation in box 302. For example, CPU 240 could perform calculations to determine whether one or more objects are present, the position of each object, and the speed of each object. Using this information and taking into account previously calculated sensing periods for the same objects, if any, CPU 240 can also determine an appropriate sensing period to be used during sensing readout; in general, the sensing period must provide an integration time shorter than the time necessary for an object to pass each cell in an array. Each object can therefore have a unique sensing period.

The operation in box 302 can also include providing any necessary signals through component I/O 244 to adjust movement of objects, such as by adjusting fluid speed; to adjust illumination or stimulation of the optical cavity; or to adjust characteristics of the optical cavity, such as by adjusting optical distances between light-reflective components or by adjusting temperature or another operating parameter of the cavity. These signals could include any appropriate combination of signals to illumination control 250, cavity control 252, and analyte control 254.

CPU 240 can then perform sensing readout on the cavity's output light, in box 304. This operation includes providing any further signals through component I/O 244 so that the cavity provides analyte-encoded output light and also providing signals through IC I/O 248 so that photons are photosensed cumulatively during the sensing period obtained in box 302. During this operation, CPU 240 may also provide signals to peripheral circuitry on an IC so that analog quantities photosensed by cells are adjusted based on reference values. After adjustment, if any, analog quantities can be converted to digital signals for readout. The operation in box 304 can be implemented in whatever manner is appropriate for a given photosensing IC, whether a CCD or CMOS implementation, and regardless of whether readout is purely serial or is also parallel.

Since an analyte's or object's optical characteristics can affect the output light provided from a mode of an optical cavity, such as in the ways described above in relation to FIGS. 1, 3, and 5, information about the optical characteristics is present in the cavity's output light, encoded in intensity functions of one or more modes. Sensing results obtained in box 304 can therefore include part or all of the encoded information. Detector 210 as in FIG. 7 can include, for example, a laterally varying transmission structure, so that a mode's intensity-energy peak in the analyte-affected output light has a respective light spot on a photosensing IC in detector 210. Therefore, the sensing results can include information about at least one of position and intensity of a light spot as shown and, accordingly, about the respective mode's intensity-energy peak. If the output light from the cavity includes intensity-energy peaks for two or more modes, their respective light spots can be tracked separately as described below. Various other techniques could be used to track an object, such as by using position and fluid speed to follow it through an extended fluidic structure, as described below.

The photosensed quantities read out in box 304 can also be digitally adjusted by CPU 240 before being stored for each tracked object, in box 306. The digital adjustment can include adjusting quantities photosensed by cells based on reference quantities, and can also include any necessary adjustments due to differences in sensing periods or other factors. The digital adjustment in box 306 and the analog adjustment, if any, in box 304 can employ reference cell techniques described in co-pending U.S. patent application Ser. No. 11/316,438, entitled "Photosensing Throughout Energy Range and in Subranges" and incorporated herein by reference in its entirety; such reference cell-based adjustment techniques may be especially useful for intensity referencing in tracking an object's position, and can, in general, be performed in relation both to measurements of refractive index and also of absorption. In particular, such adjustments can be used to overcome problems with inhomogeneous illumination, but such techniques may be difficult to implement successfully in system 200 because external inhomogeneities that affect output light, such as in illumination or in stable or time-varying absorption by particles between light sources 220 and optical cavity 204, are not readily distinguishable from absorption within cavity 204. In other words, adjustment based on reference cells may remove desired information about absorption changes inside cavity 204.

To avoid this and other such problems, the operation in box 306 or a subsequent operation can make an alternative data manipulation or adjustment to obtain "cavity-only absorption data", an expression that refers herein to values or other data in which information about absorption in cavity 204 is preserved while information is reduced about features exterior to cavity 204 such as inhomogeneities in illumination and external absorption, as described in co-pending U.S. patent application Ser. No. 11/702,249, entitled "Obtaining Information From Optical Cavity Output Light" and incorporated herein by reference in its entirety. As will be understood, the encoding of absorption information in the manner described herein allows removal of noise-like effects other than those from absorption coefficient inside cavity 204, influences such as external perturbations, disturbances, or inhomogeneities. As a result, measurements of absorption can have a higher signal to noise ratio. Also, information can be recovered from analyte-encoded output light that is selectively sensitive to absorption changes inside cavity 204.

The position and speed information about each object from box 302 can be used by the operation in box 306 to track each trackable object and determine which photosensed quantities result from effects of each tracked object. Similar techniques can be used to determine which photosensed quantities result from each mode's light spot when a cavity's output light includes two or more modes.

For homogeneous analyte in cavity 204 or for stationary or slow-moving objects in cavity 204, lock-in techniques could be applied to further improve signal to noise ratio, such as by modifying operations in boxes 302, 304, and 306 in FIG. 9. For example, illumination from light sources 220 can be modulated in order to modulate output light from cavity 204. The applicable modulation frequencies would be constrained by the readout frequency achievable by detector 210. In implementations where it is not possible to directly record a correlation signal, a self-reference could be used, such as an empty channel in a fluidic structure or an uncoated reference cell in a photosensing array with coated cells to sense photon energy subranges.

In performing the operations in boxes 304 and 306, CPU 240 can employ data structures (not shown) stored in memory 246. For example, one data structure can store each trackable object's previously calculated position and speed, which can then be used in performing subsequent calculations to track the object and identify its effects; similarly, each object's data structure can also include each light spot's identifying information and the object's effect on the identified light spot, which can similarly be used in subsequent calculations. Also, a readout data structure can be employed to hold all of the adjusted quantity information about each object.

The operation in box 306 can update the readout data structure each time it obtains additional information about the same tracked object. In an implementation as in FIG. 8, the operations in boxes 300, 302, 304, and 306 can be performed separately for each of ICs 260 through 262. Further, as suggested by the dashed line from box 306 to box 300, the same operations can be performed repeatedly for each of the ICs. If each object can be correctly identified and tracked throughout its travel along a path through cavity 204, the readout data structure can be used to hold all of the information obtained from all ICs. Between consecutive executions of the operations in boxes 300, 302, 304, and 306, the effects of each tracked object may move only a few cells along the path, and consecutive objects must be sufficiently separated to avoid confusion. For example, each object may be a few μm in diameter, each cell may have a length along the path of between 10 and 20 μm, and consecutive objects may be two or three cell lengths apart. For larger objects or for cells of different sizes, the spacing between consecutive objects can be adjusted appropriately.

Various modifications could be made in the implementation of FIG. 9. For example, rather than being spaced apart, objects could be closer together. Even if several objects are having overlapping effects on a light spot, it may be possible to perform computational algorithms to separate the effects of the objects. Similarly, if objects are very close to each other but positioned along different cells, an optical structure between the path of the objects and detector 210 could ensure that photons affected by different objects travel to different cells; in this way, a continuous stream of objects could be measured. Furthermore, techniques as described above could be applied to a continuous fluidic stream without distinguishable objects in it, in which case the analyte-affected output light from optical cavity 204 would be determined by optical characteristics of concentrations of molecules in each position in the stream rather than by optical characteristics of distinguishable objects. In effect, the stream would be divided into imaginary small volumes, each of which would be an object analyzed as described above, allowing for continuous monitoring of how the output light from the fluid changes with time, such as due to changing composition of the fluid.

As the operations in boxes 300, 302, 304, and 306 are repeated while an object travels along a path past detector 210, more and more information is obtained, especially where a cavity's output light has more than one light spot, with each light spot having a respective position on the array. When the object has passed the whole array, information about the tracked objects it contains can be recomposed from the stored fractions.

Upon completion of any suitable amount of information gathering in boxes 300, 302, 304, and 306, CPU 240 can perform the operation in box 310 to use analyte information to distinguish objects. As shown, this operation can include combining the sensed quantities for each object so that analyte information for the object can be provided, such as in the form of an absorption spectrum, a value for the refractive index of analyte in the object, or some other data structure.

Counting of cancerous cells and sorting rare cells are specific examples of object distinguishing operations that CPU 240 might perform in box 310. For each tracked object, the analyte information could include values for its optical characteristics. Then, based on stored values for different types of cells, similar to those in Table 1 above, tracked objects having optical characteristic values that match each type of cells could be counted. If refractive index as in Table 1 does not permit satisfactory discrimination, a combination of refractive index and absorption might be satisfactory, or some other combination of two or optical characteristics, possibly all obtained by CPU in performing the routine in FIG. 9 or obtained by a combination of operations, including other ways of obtaining information about objects as described in co-pending U.S. patent application Ser. No. 11/315,992, entitled "Sensing Photons from Objects in Channels" and incorporated herein by reference in its entirety. If it is possible to obtain sufficient information to perform a satisfactory discrimination, such counts could be used, for example, for diagnostic purposes.

FIG. 10 shows device 350, which could be used in an implementation of system 200. Entry glass 352 and an exit glass (not shown) are of substantially the same size and shape, and their inward-facing surfaces have coatings or other structures that function as light-reflective components, reflecting light into a light-transmissive region between them to operate as an optical cavity. The two glasses are illustratively separated by spacers 354 and the light-transmissive region may also contain fluidic walls or other structures (not shown) that bound a duct or channel between inlet 356 and outlet 358; as a result, an analyte or a fluid carrying an analyte can enter the optical cavity from inlet 356, can be carried along a path through the optical cavity such as through a duct or channel, and can then exit from the optical cavity to outlet 358.

Over or on entry glass 352 is light source component 360, which can include one or more light sources such as lasers, LEDs, or super luminescence diode (SLDs) to illuminate the optical cavity. Photosensing array 362 is on the underside or below the exit glass, positioned along the analyte's path through the optical cavity. Light source component 360, array 362, and the optical cavity between them have characteristics such that the optical cavity responds to illumination from the light sources by providing analyte-affected output light that can be photosensed by array 362.

FIG. 11 shows a longitudinal cross-section of device 350, viewed along the line 11-11 in FIG. 10. In the illustrated cross-section, light sources 360 are providing light, represented by arrows 380, which passes through entry glass 352 and through entry light-reflective structure 382 before entering channel 384. Within channel 384, a moving fluid such as a liquid, gas, or aerosol, represented by arrows 390, carries an object 392. While object 392 is present in the optical cavity, its optical characteristics can affect light reflected within channel 384 between entry light-reflective structure 382 and exit light-reflective structure 394. As a result, analyte-affected output light exits through exit light-reflective structure 394 and is transmitted through exit glass 396 and then transmission structure 398 before being photosensed by array 362.

In general, object 392 can be a particle, droplet, or small volume of fluid that can be carried by a fluid or other appropriate substance and that includes an analyte to be analyzed.

The terms "fluidic structure" and "channel" are used herein with related meanings: A "fluidic structure" is a structure that depends for its operation on fluid positioning or fluid flow, such as, for liquids or gases, in response to pressure or, for liquids, as a result of surface tension effects; a "channel" is any tube or other enclosed passage defined within a fluidic structure and through which fluid flows during operation. The direction in which fluid flows within a channel is sometimes referred to herein as a "flow direction."

Transmission structure 398 can be an LVF implemented as described above in relation to FIG. 4 or can be any other appropriate transmission structure with a suitable laterally varying energy output function, so that incident light on array 362 similarly has a "laterally varying photon energy distribution" or simply a "laterally varying energy distribution", meaning that photon energy of incident light varies as a function of lateral position. For example, transmission structure 398 can provide a laterally varying energy distribution on array 362 by transmitting, at each position along channel 384, only light in a respective narrow subrange of photon energies, with the respective subranges being different at different positions along channel 384. Therefore, for each position, a respective set of one or more cells of array 362 receives light only if the position's respective subrange includes or overlaps with a subrange in which the optical cavity is providing output light, such as the subrange of an intensity-energy peak as illustrated in FIG. 4.

A detector or other device or apparatus including both transmission structure 398 and array 362 could be implemented in a wide variety of ways, some of which are described in co-pending U.S. patent application Ser. No. 11/315,386, entitled "Sensing Photon Energies Emanating from Channels or Moving Objects," and incorporated herein by reference in its entirety. For example, array 362 could have a photosensitive surface with an appropriate pixel- or cell-density and transmission structure 398 could be a coating over the photosensitive surface that operates as an LVF.

Array 362 could be implemented with any appropriate readout technique, such as CMOS or CCD readout, for which cell dimensions of 5-50 μm are currently typical, and smaller cell dimensions are foreseeable. Although array 362 could be a one-dimensional array with a line of cells parallel to the flow direction of arrows 390, implementation with a two-dimensional array could beneficially provide, at each position along the path of object 392, a set of two or more cells in a line perpendicular to the flow direction, with all the cells in the set concurrently photosensing incident light in the same photon energy subrange; sensing results from each set of cells could be used to average or otherwise combine and improve information obtained for a given transmission mode's output light.

Entry and exit light-reflective structures 382 and 394 operate as two parallel mirrors, with channel 384 being a light-transmission region between them, providing an optical cavity as described above. With appropriate parameters, the cavity can operate as a Fabry-Perot interferometer, and its transmission properties will be determined by the mirrors and the region between them: The mirrors affect FWHM of peaks of the cavity's transmission spectrum and their reflectivity also affects the quality of the stop-band, i.e. how much light is transmitted outside of transmission modes. Also, the refractive index and distance between structures 382 and 394 affect or determine the photon energies that are transmitted by the optical cavity.

Each of structures 382 and 394 can be implemented as a layered structure with alternating dielectric layers or with metal, deposited in either case on entry glass 352 and exit glass 396. Rather than glasses 352 and 396, the enclosing walls of channel 384 through which light enters and exits could instead be implemented with any other suitable light-transmissive components with inward-facing surfaces that are or can be made reflective, such as by fabrication of appropriate structures on them.

In an illustrative implementation, light source 360 illuminates the optical cavity homogeneously with a collimated light beam from a suitable light source, such as an LED, broadband laser, or superluminescence diode (SLD); suitable optical components can be used to spread a light beam to illuminate all of array 362, such as with spreading components as disclosed in co-pending U.S. patent application Ser. No. 11/315,387, entitled "Propagating Light to be Sensed" and incorporated herein by reference in its entirety. In other implementations, light source 360 could include or be replaced by an array of light sources, reducing or eliminating the need for spreading. For example, a single broadband light source like an LED or SLD could be replaced by an array of laser diodes (not shown) or narrow-band emitting LEDs (e.g. resonant cavity LEDs), each emitting at a respective wavelength; this approach could beneficially increase the interaction length between light and analyte in larger cavities in which interaction length is limited by a light source's coherence length. In addition, since different positions of transmission structure 398 transmit different photon energy subranges, each laser diode in the array could beneficially be positioned or oriented to illuminate a respective position at which transmission structure 398 transmits the diode's emission wavelength.

If object 392 is absent and fluid in channel 384 is homogeneous, device 350 can operate as a homogeneous optical cavity as described above in relation to FIGS. 2 and 3. The output light from the optical cavity can include one or more discrete transmission modes if the dimensions and refractive index of the optical cavity are appropriate. The presence of object 392, however, can change the refractive index and absorption of the optical cavity due to optical characteristics of object 392. For example, if object 392 has a certain absorption spectrum, it can affect the intensity amplitude Imax and the FWHM of each transmitted mode as illustrated in FIG. 3 and also its contrast as described above; similarly, the refractive index of object 392 can affect photon energies of the modes as illustrated in FIG. 3. These are examples of "encoding information" about optical characteristics, an expression used herein to refer to any operation or combination of operations by which an optical cavity's output light is modified in a way that depends on optical characteristics, such as of object 392.

In response to output light from the optical cavity, array 362 can accordingly obtain sensing results that indicate changes in the central energy, intensity amplitude, contrast, and FWHM of each transmitted mode, providing information about object 392 and its effect on the refractive index and absorption in the optical cavity. The sensing results can then be used, such as by CPU 240 in executing analyte information routine 274 to "obtain information", an expression used herein to refer to any operation or combination of operations performed on sensing results from photosensing an optical cavity's output light and that produce indications of information encoded in the output light; the indications could, for example, be electrical signals, data stored by an appropriate memory device, displayed information, and so forth. For example, sensing results that indicate intensity, FWHM (or other intermediate intensity width), contrast (e.g. Tmax/Tmin or other suitable value), or any other relevant measurable feature of each transmitted mode can be used to obtain data indicating an absorption value for a given photon energy such as the central wavelength of the mode; similarly, sensing results indicating central energy shift can be used to obtain data indicating a refractive index value for the optical cavity with object 392 present.

An alternative approach could encode information about optical characteristics in reflection modes of a Fabry-Perot cavity rather than in transmission modes. Sensing results from reflection modes could be used, for example, to obtain information about absorption spectra and refractive index dispersion. This approach could be beneficial in applications where improved readout sensitivity is desirable: As described above in relation to box 36 in FIG. 1, analyte could fill or otherwise be positioned within a slightly asymmetric Fabry-Perot cavity designed so that the cavity with analyte approximates a symmetric Fabry-Perot cavity, which would be true for a cavity of width w and absorption α if the second mirror's effective reflectivity Reff(2) is substantially equal to the first mirror's reflectivity R(1) as follows:

$$Reff(2) = R(2) * \exp(-2\alpha w) = R(1)$$

In some implementations of system 200, object 392 would be a biological cell carried by liquid flowing through channel 384, and device 350 could be used to encode information about optical characteristics of a series of such cells and to obtain sensing results indicating the encoded information; information about the optical characteristics could then be obtained from the sensing results by CPU 240 and used in an appropriate way, such as for the purpose of distinguishing types of biological cells. In encoding and obtaining information about refractive index, for example, the information will result not only from a biological cell but also from the fluid or other medium that is carrying it and fills channel 384 around the cell. The resulting measured refractive index will therefore be a combination between that of the fluid and that of the biological cell. If the size of the cell is known, its actual refractive index could be determined from the measured refractive index; the size of the cell can be determined, for example, by using a Coulter counter and/or a light scattering unit, such as an MIE scattering device.

Figure 12:
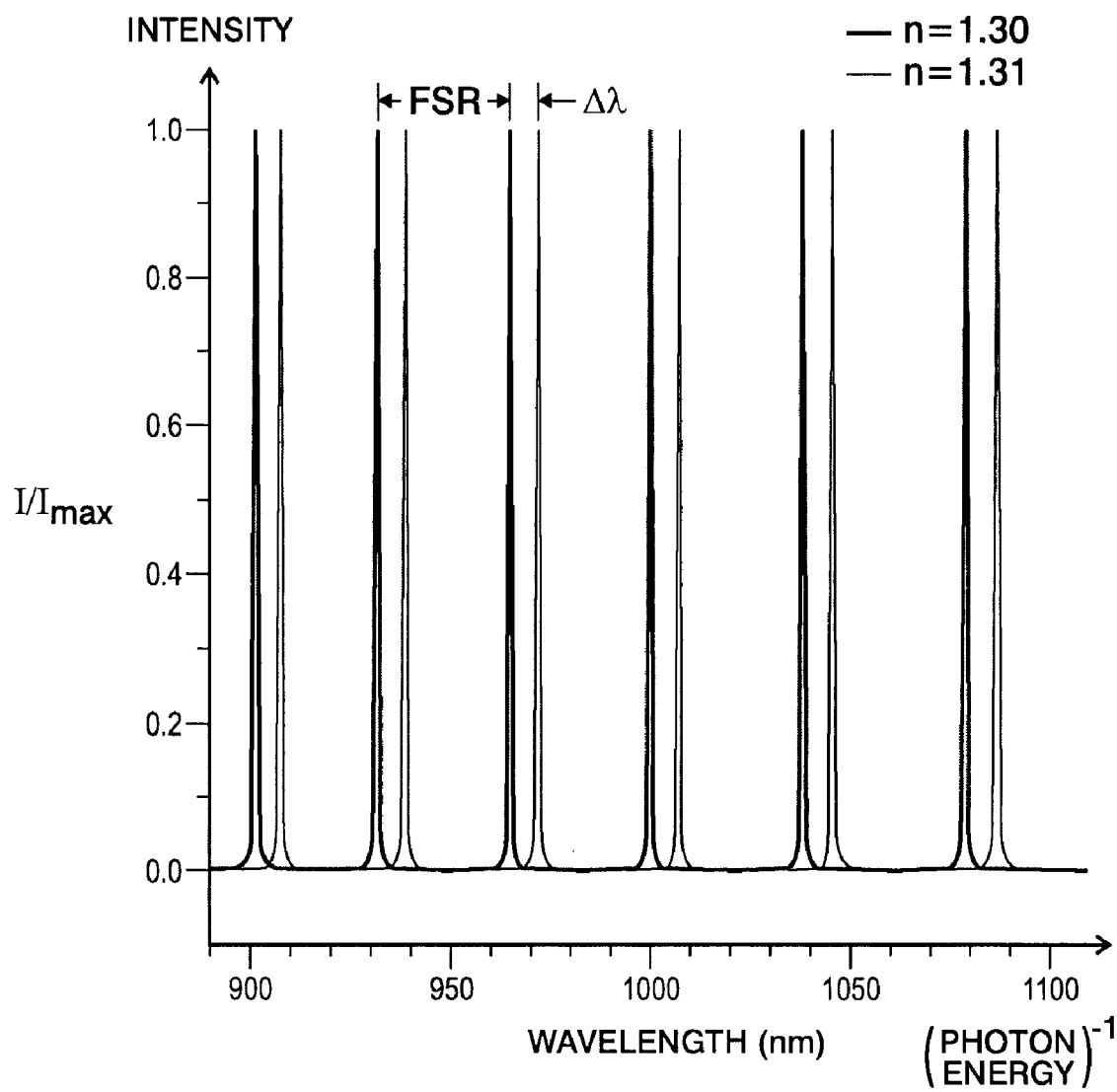
FIG. 12 is a graph showing two transmission spectra that could be obtained from a device as in FIGS. 10 and 11 with analytes having different refractive indices.

FIG. 12 shows two transmission spectra that illustrate how a change in refractive index shifts transmission peaks. The illustrated portion of the spectra includes six pairs of peaks near a wavelength of 1.0 μm. In each pair, the leftward peak was obtained with a refractive index of 1.30 while the rightward peak was obtained with a refractive index of 1.31. In both cases, the width w of the cavity operating as a Fabry-Perot interferometer was 10 μm. As can be seen, the FSR is approximately 37 nm, while the shift Δλ resulting from the refractive index change of 0.01 is approximately 8 nm. This is consistent with the following equations for the case of incident light parallel to the reflection direction:

$$FSR = \lambda(k) - \lambda(k+1) = 2nw/k(k+1) \stackrel{k \to \infty}{\approx} (\lambda(k))^2 / 2nw$$

and $$\Delta\lambda(k) = 2\Delta nw/k.$$

In general, the first of these equations shows that FSR becomes smaller, and transmission peaks therefore become closer, as w increases. Also, a slight increase in n causes a slight increase in FSR. These effects, however, are not readily visible in FIG. 12.

In designing device 350 to encode information about optical absorption and to obtain sensing results indicating such information, several constraints must be taken into account—the desired absorption or interaction length; the desired volume of analyte; the required photon energy range and resolution for absorption spectra; the wavelength resolution of the detector that includes transmission structure 398 and array 362; and so forth. To reach a suitable compromise between these constraints, several parameters can be adjusted, including the width of the cavity, the reflectivity of the mirrors, size of array 162, properties of transmission structure 398, and possibly absorption within the cavity, though absorption is not easily adjusted.

Device 350 as in FIGS. 10 and 11 can also be used to encode information about a homogeneous analyte such as a liquid, gas, or aerosol, within channel 384 without the presence of object 392. For example, a single readout of sensing results from array 362 can provide information about the transmission spectrum of the homogeneous analyte. If the analyte changes on a relatively long time scale compared to transit time through device 350, sensing results read out at different times can indicate long-term changes of the transmission spectrum. For this approach, however, accurate measurements can only be obtained if the analyte present within channel 384 during a given readout is substantially homogeneous.

Figure 13:
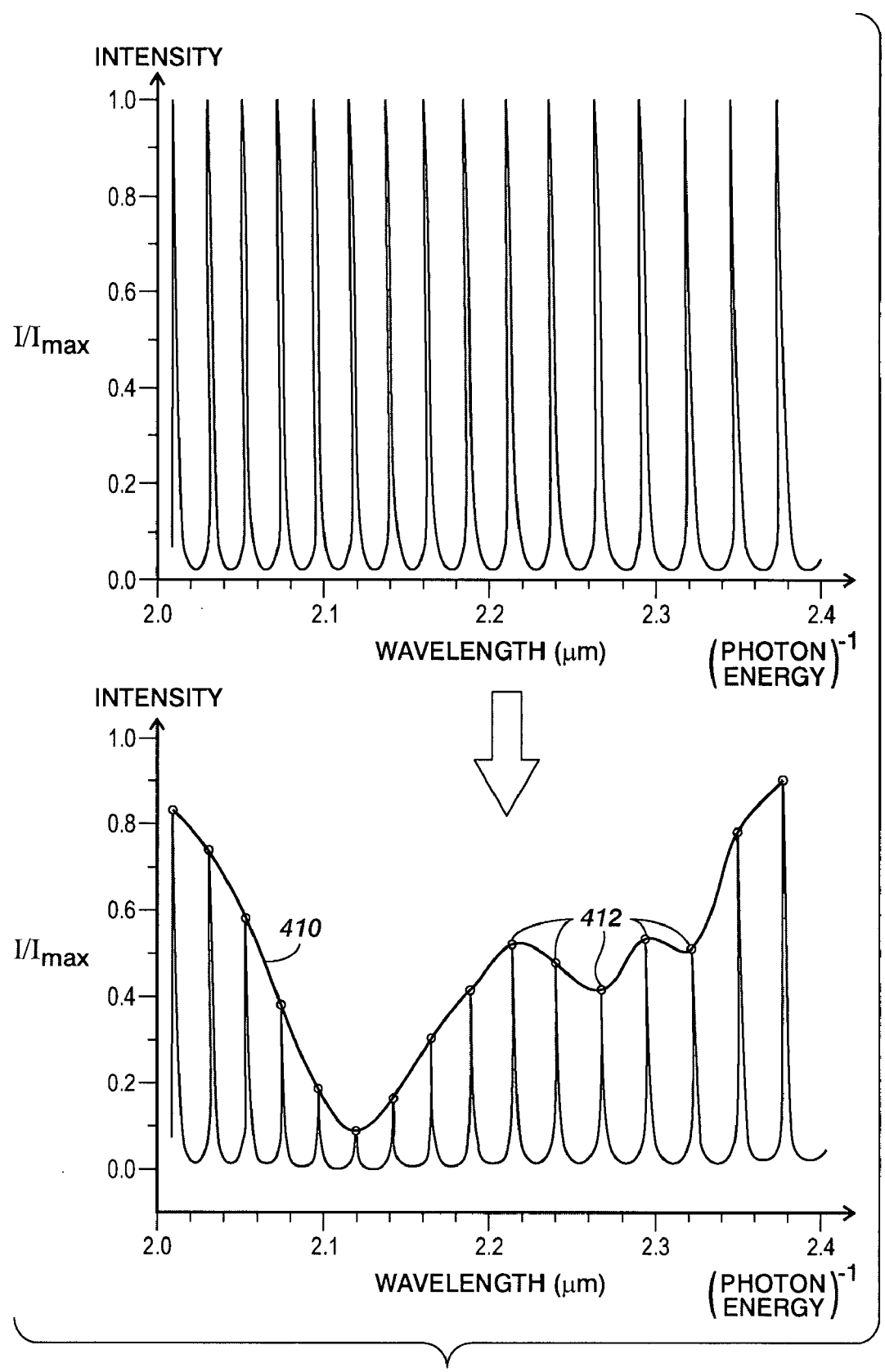
FIG. 13 includes two graphs showing two transmission spectra that could be obtained from a device as in FIGS. 10 and 11 with an analyte absent and present, with the second graph providing an absorption spectrum for the analyte.

FIG. 13 illustrates graphically the effect an analyte can have on a Fabry-Perot interferometer's transmission spectrum. The cavity illustratively has a width w of 75 μm and a mirror reflectivity of 95%. Without analyte present in the cavity, each of the illustrated transmission modes transmits light to a normalized intensity amplitude of 1.0, as shown in the upper part of FIG. 13.

With the analyte present, in this case glucose in water, transmission of nearly all modes is decreased due to absorption, with the resulting peaks for the illustrated modes falling on curve 410 in the lower part of FIG. 13. Curve 410 can therefore indicate the absorption spectrum of the analyte, with the circles 412 serving as discrete sampling points of the absorption spectrum. In order to measure the absorption spectrum to a desired resolution, the cavity width w and other parameters must be chosen to obtain a sufficient number of sampling points.

FIG. 13 also suggests that increased glucose absorption dramatically reduces intensity of a mode because of the strongly enhanced interaction length that occurs within a cavity with highly reflective mirrors. This means that light bounces back and forth within the cavity many times before being transmitted. As described above, the increased analyte absorption also causes broadening of the modes. The larger the absorption, the smaller the mode's intensity and contrast and the larger the mode's FWHM (or other intermediate intensity width); the lower part of FIG. 13 suggests but does not fully show the change in FWHM that would occur. Additional details about effects of absorption are provided in co-pending U.S. patent application Ser. No. 11/702,363, entitled "Encoding Optical Cavity Output Light" and incorporated herein by reference in its entirety.

As suggested by arrows 390 in FIG. 11, object 392 can move at a relatively uniform speed along a path within channel 384. As a result, its effect on transmission modes of the optical cavity will also follow a path, allowing correlation between sensing results from array 362 and the position of object 392, such as with the techniques described in co-pending U.S. patent application Ser. No. 11/315,386, entitled "Sensing Photon Energies Emanating from Channels or Moving Objects" and incorporated herein by reference in its entirety. In effect, a series of cells in array 362 obtain sensing results that include information about optical characteristics of object 392. These sensing results can be used to obtain information as described herein.

In the specific example illustrated in FIG. 11, absorption spectroscopy could be performed, for example, by obtaining sensing results as object 392 moves through channel 384, using the sensing results to obtain actual absorption values of object 392 for each transmission mode based on biological cell size and flow velocity, and composing an absorption spectrum using the actual values obtained. This technique takes advantage of the motion of object 392 for improved detection, and also enables large integration times without losing throughput capacity. Highly sensitive optical absorption spectroscopy can be performed in this manner.

FIGS. 14-15 show device 440, an alternative implementation with features similar to those shown in FIGS. 10-11, but with multiple channels 450, 452, 454, 456, and 458 bounded by walls 460 and with a flow direction indicated by arrows 462. A single two-dimensional photosensing array 470 can obtain sensing results for all the channels, with sets of cells providing sensing results in the manner described above for two-dimensional arrays. Biological cells or other objects, represented by the shaded circles such as circle 472, can be correlated with their sensing results based on flow velocity, as described above.

FIG. 15 shows a cross-section of device 440 taken along the line 15-15 in FIG. 14. As in FIG. 11 above, light sources 480 could be implemented in any appropriate way to illuminate channels 450 through 458. Entry glass 482 could have entry light-reflective component 484 formed on its inward-facing surface as described above, and exit glass 494 (or another substrate that can carry a mirror) could have exit light-reflective component 492 formed on its inward-facing surface. Transmission structure 490 could be formed on array 470.

Transmission structure 490 could be implemented in any of several different ways to provide desired sensing results. For example, transmission structure 490 could be a layered structure, implemented with any of the techniques described in co-pending U.S. patent application Ser. No. 11/316,303, entitled "Obtaining Analyte Information" and incorporated herein by reference in its entirety.

In one exemplary implementation, transmission structure 490 could be an LVF that is graded in the x-direction shown in FIG. 14 but is homogeneous in the y-direction. In this case, array 470 would be sensitive to the same photon energy subrange in all of channels 450 through 458. Therefore, information about the same changes in refractive indices and absorption information could be obtained from all the channels, with parallel positions in the channels providing information about the same photon energy subranges. Since the subranges vary along each channel, information can be obtained for a number of different subranges or for an entire spectrum as a biological cell or other object is carried through a channel. In this case, all channels are identical and objects or analytes are characterized in the same manner independent of the channel through which they are passing.

In another exemplary implementation, transmission structure 490 could be an LVF that is graded in the y-direction in FIG. 14 but homogeneous in the x-direction. This arrangement could be obtained, for example, by rotating the previously described exemplary implementation through 90°. In this case, a set of two or more cells that extend in a line across a channel at a certain position will receive different photon energy subranges, so that the intensity ratio between cells in such a set will change as a biological cell or other object passes by while being carried through the channel. In this case, refractive index change of an object can be recorded as a function of time while it is moving along the channel, or multiple measurements or longer integration times (in the case of a homogeneous analyte) can be used to increase sensitivity. Note that in parallel channels different modes are used to determine refractive index.

In yet another exemplary implementation, transmission structure 490 could be graded in both the x-direction and the y-direction. This case would allow information to be obtained about different subranges in both of the ways described above.

In general, various referencing techniques could be used to measure optical characteristics such as absorption spectra and refractive index values by comparison to reference values obtained from the same optical cavity, such as with a known reference solution or other fluid. In the implementation in FIGS. 14 and 15, for example, every other channel, such as channels 452 and 456, could serve as a reference channel if it is empty or contains only a known homogeneous reference fluid, allowing more precise evaluation of absorption spectra and dispersion of the refractive index in channels 450, 454, and 458, such as by comparing measured analyte values with measured reference values; for example, to sense glucose concentration based on optical characteristics, the reference medium could be a known glucose concentration. Since reference medium and analyte are moving within the same environment or channel system this also allows compensation for external influences (like temperature, pressure, etc.) that may have a significant influence on optical properties.

Figure 16:
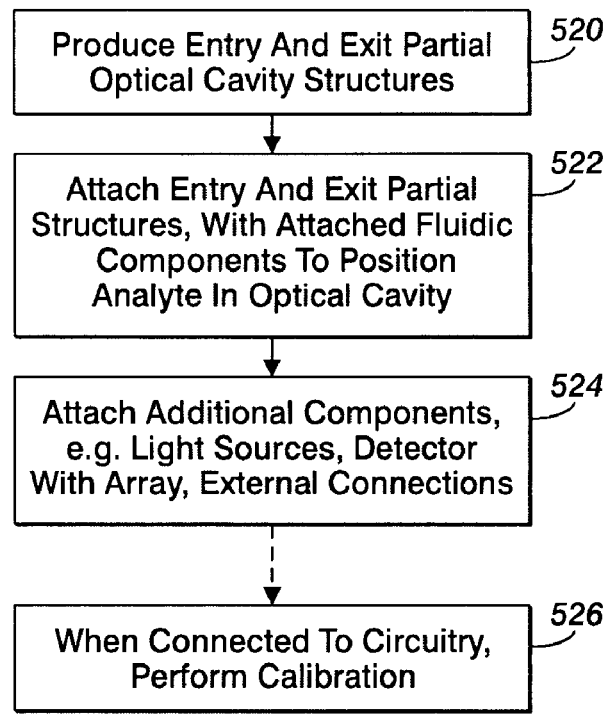
FIG. 16 is a flowchart showing operations in producing devices as in FIGS. 10, 11, 14, and 15.

FIG. 16 illustrates exemplary operations in producing a device like device 350 in FIGS. 10 and 11 or device 440 in FIGS. 14 and 15. In particular, the operations in FIG. 16 make it possible to produce apparatus in which information about optical characteristics of an analyte can be encoded and sensing results indicating the information about the optical characteristics can be obtained.

The operation in box 520 in FIG. 16 produces entry and exit partial optical cavity structures. This operation can include producing entry light-reflective structure 382 on entry glass 352 and also producing exit light-reflective structure 394 on exit glass 396, both as in FIG. 11. Similarly, this operation can include producing entry light-reflective component 484 on entry glass 482 and also producing transmission structure 490 and exit light-reflective light component 492 on photosensing array 470 as in FIG. 15. This operation can also include producing a patterned layer of SU-8 or polydimethylsiloxane (PDMS) on one or both of the light-reflective structures, such as with techniques described in co-pending U.S. patent application Ser. No. 11/315,992, entitled "Sensing Photons from Objects in Channels" and incorporated herein by reference in its entirety. This patterned layer could include structures such as spacers 354 in FIG. 10 and walls 460 in FIGS. 14 and 15. If appropriate, an anti-adhesive coating can be applied to interior channel surfaces, such as by dip-coating polyethylene glycol (PEG) or by providing a coating of parylene C or vapor deposited tetraglyme.

The operation in box 522 then attaches the entry and exit partial structures, with attached fluidic components to position analyte in the resulting optical cavity. The operation in box 522 can include forming a suitable bond between the entry and exit partial structures so that they are firmly attached to each other. Also, the fluidic components attached to the resulting optical cavity structure can include, for example, connectors, tubing, pumps, sensors, and so forth; it is important that the combination of fluidic components be capable of operating to cause and control positioning of analyte within the optical cavity, such as by carrying the analyte into the optical cavity with a fluid or in some other way. The operation in box 522 can also optionally include attachment of wires or other appropriate circuitry connected, for example, to the photosensing array.

The operation in box 524 then attaches any other additional components necessary to complete the device. For example, if the device includes light sources, such as light source component 360 in FIGS. 10 and 11 or light sources 480 in FIG. 15, these components can be attached by the operation in box 524. Similarly, if a detector that includes a photosensing array and a transmission structure is not part of the exit partial structure, as in FIG. 15, the detector can be attached by the operation in box 524. The operation in box 524 can also include any other external electrical, optical, or fluidic connections necessary for operation of the device. Alternatively, such connections could later be made when the device is incorporated into a system, such as system 200 in FIGS. 7 and 8.

The operation in box 526 can be performed at any appropriate time after the other operations, as suggested by the dashed line from box 524 to box 526. In addition, the operation in box 526 performs calibration, which requires that components be appropriately connected to circuitry, such as in the ways illustrated in FIGS. 7 and 8. The necessary connections could be created as part of the operations in boxes 520, 522, and 524 or instead could be created after the operation in box 524 and before performing calibration. In any case, calibration in box 526 can include obtaining items of data or data structures to be used in obtaining analyte information as described herein, and the data or data structures can be stored in memory 246 as part of calibration data 276 (FIG. 8), or, in appropriate cases, can be embedded in analyte information routine 274 or stored in another appropriate form.

In general, the operations in any of boxes 520, 522, 524, and 526 can include additional activities. For example, at any appropriate point in production of the device, wires or other appropriate circuitry can be attached to provide signals to or from a microprocessor or input/output (I/O) device to pumps and other fluidic components or to provide signals from a photosensing array to a microprocessor or I/O device. Similarly, connections can be made at any appropriate time to provide power.

The technique of FIG. 16 could be modified in many ways within the scope of the invention. For example, the operations in boxes 520, 522, and 524 could be combined in any appropriate way to facilitate attachment of components in a desired sequence. Also, an additional operation could be performed to align or attach interconnects between ICs, gates, and other circuitry, such as connectors to a microprocessor or computer, or this operation could be partially performed in each of boxes 520, 522, 524, and 526. Furthermore, the technique of FIG. 16 is extremely general, and could be employed to produce a wide variety of different devices that encode information about optical characteristics of analyte within an optical cavity and obtain sensing results indicating the optical characteristics. The examples illustrated in FIGS. 10, 11, 14, and 15 above show how objects can be carried through a channel within an optical cavity while such operations are performed, but various other arrangements are possible, some examples of which are described below.

Figure 17:
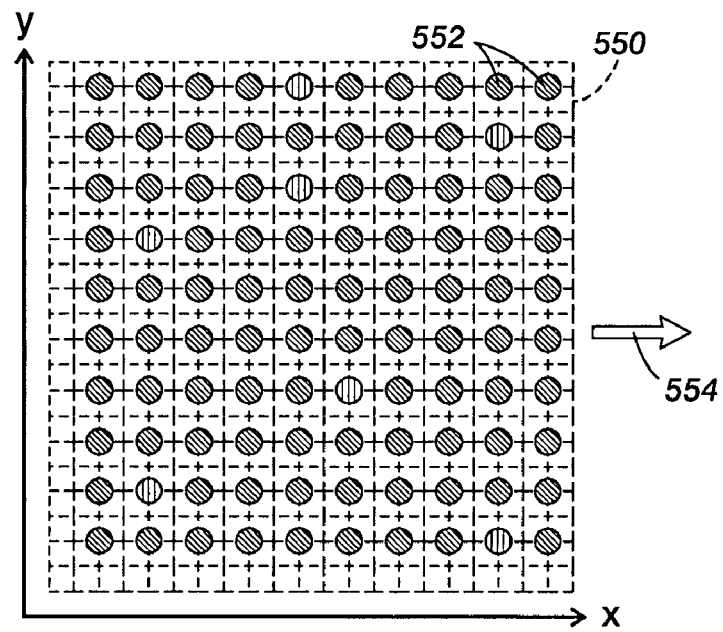
FIG. 17 is a schematic top view of components of an implementation of a system as in FIGS. 7 and 8 in which relative motion occurs between a biochip with an array of analyte-containing wells or locations and a photosensing array.

FIG. 17 illustrates a different type of implementation in which relative movement between analyte and photosensing array occurs, but in a manner different from the implementation in FIGS. 14 and 15. Photosensing array 550 moves relative to a biochip with an array of wells each of which can contain analyte or another fluid, such as a reference fluid; each well is represented in FIG. 17 by a shaded circle, such as circle 552. Relative motion between array 550 and the biochip is indicated by arrow 554. The biochip can, for example, be sandwiched between two mirrors (not shown) so that each well is within the optical cavity formed between the mirrors, and the cavity can be illuminated in any of various ways; the illustrated technique makes it unnecessary to perform scanning illumination, since illumination and sensing can be fully parallel. In the case, for example, in which the biochip is moved in the x-direction as indicated by arrow 554 and in which a transmission structure (not shown) over array 550 is an LVF with a gradient in the x-direction but homogeneous in the y-direction, each of the wells can pass along a respective path across the array along which sensing results are obtained for each photon energy subrange of a spectrum, allowing for step-by-step spectral characterization of the contents of each well. The wells can be correlated with their respective sensing results based on the relative velocity, similarly to the techniques described above. After all sensing results are obtained, a deconvolution of the sensing results can be performed to obtain the absorption spectrum and refractive index dispersion for each well of the biochip.

The techniques illustrated in FIGS. 14, 15, and 17 are only a few of the many possible ways of implementing relative motion between analyte in an optical cavity and a photosensing component. Additional techniques are described in co-pending U.S. patent application Ser. No. 11/702,470, entitled "Moving Analytes and Photosensors" and incorporated herein by reference in its entirety. As indicated by techniques described there and above, objects in channels and wells could be distinguished as they move relative to a photosensing array. In general, all techniques described herein by which objects are distinguished could be performed in combination with relative motion that provides a stream of objects to be distinguished, including locating, counting, sorting, selecting, directing, separating, and determining paths of objects. Information about each object can be obtained in sequence, making it possible to distinguish objects based on correlations between objects and information obtained about them.

FIG. 18 shows setup 600, a combination of components that can be used in a system as in FIGS. 7 and 8, but possibly without an optical cavity structure as defined above; instead, a combination of components could operate as a laser cavity even though they may not be connected into a structure. Laser mirrors 602 and 604 provide reflection surfaces for the laser cavity, and gain medium 606 provides laser amplification. Duct 610, shown in dashed lines, represents a path along which objects can be carried through the laser cavity, with objects 612, 614, and 616 illustratively being carried in the direction indicated by arrows 618; objects 612, 614, and 616 could, for example, be small volumes of fluid, biological cells, or any other type of particle or object as described above.

As a result of the presence of any of objects 612, 614, and 616 in the laser cavity, emitted light represented by arrows 620 includes information about optical characteristics of analyte. Possibly after a spreading operation as described in co-pending U.S. patent application Ser. No. 11/315,387, entitled "Propagating Light to be Sensed" and incorporated herein by reference in its entirety, the analyte-affected output light is transmitted through transmission structure 622, which can be an LVF, and is photosensed by photosensing array 624. Setup 600 therefore makes it possible to obtain information, for example, about refractive index of objects 612, 614, and 616, because a change in refractive index in the laser cavity causes a shift of the emitted laser wavelength, in the manner described by Liang X. J., Liu, A. Q., Zhang, X. M., Yap, P. H., Ayi, T. C., and Yoon, H. S., "Refractive Index Measurement of Single Living Cell Using a Biophotonic Chip for Cancer Diagnosis Applications," 9$^{th}$ International Conference on Miniaturized Systems for Chemistry and Life Sciences, Oct. 9-13, 2005, Boston, Mass., 2005, pp. 464-466.

Setup 600 can be implemented, for example, with an external cavity laser diode. A detector that includes transmission structure 622 and array 624 can be implemented in any of the ways described above to obtain an inexpensive, compact structure that can very precisely and rapidly sense the shift of emitted laser wavelength resulting from refractive index change. By simultaneously monitoring the intensity of the laser output, analyte-induced cavity loss, such as absorption at the laser wavelength, can be recorded.

FIG. 19 shows device 650, which can also be used in a system as in FIGS. 7 and 8, such as to obtain information about optical characteristics of tracked objects, such as refractive index and absorption. Light-reflective structures 652 and 654 provide reflection surfaces on either side of region 656, which can be filled with analyte as shown. As a result, when input light, represented by arrows 658, is received through structure 652, optical cavity operation can occur, resulting in transmission of light to photosensing component 660. The index of refraction of analyte in region 656 and the positioning of structures 652 and 654 determine positions of light transmission, and illumination can be provided so that only certain wavelengths are transmitted, one of which is represented by arrow 662.

Figure 20:
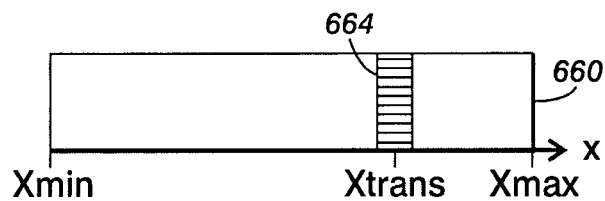
FIG. 20 is a schematic top view of a photosensing component as in FIG. 19.

FIG. 20 shows an example of the pattern of light on the upper surface of photosensing component 660 if the optical cavity were illuminated in only one narrow wavelength band. As shown, light spot 664 on photosensing component 660 indicates that the incident narrow band light is transmitted at a certain position Xtrans. If analyte refractive index changes, the location of the transmitted light spot 364 would move, either toward Xmin or Xmax. If analyte absorption changes, causing a change in intensity and FWHM of output light's intensity function, the size and intensity of light spot 364 would change.

Inhomogeneous optical cavities that contain analyte can be implemented in many ways in addition to the way illustrated in FIGS. 19 and 20. Additional techniques are described in co-pending U.S. patent application Ser. No. 11/702,325, entitled "Containing Analyte In Optical Cavity Structures" and incorporated herein by reference in its entirety. In many applications, an optical cavity structure as in FIGS. 1 and 7 could be implemented to include one or more inhomogeneous optical cavities that contain analyte as in FIGS. 19-20. Furthermore, the optical cavity in device 650 could instead be a homogeneous optical cavity that contains analyte and that is operated to provide a laterally varying output energy distribution, by providing a range of angles at which input light is incident, as described in co-pending U.S. patent application Ser. No. 11/316,438, entitled "Photosensing Throughout Energy Range and in Subranges" and incorporated herein by reference in its entirety.

Figure 21:
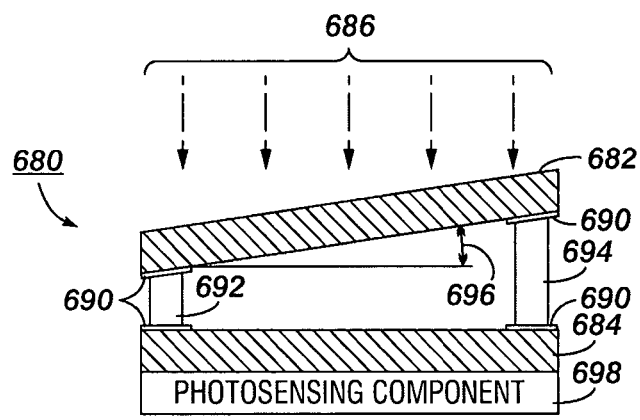
FIG. 21 is a schematic side view of an optical cavity that can be tuned by modifying the length of elastomer spacers and could be used in a system as in FIGS. 7 and 8.

FIG. 21 shows device 680, which can also be used in a system as in FIGS. 7 and 8, such as to produce an inhomogeneous optical cavity as in FIG. 19 or to produce a tunable homogeneous or inhomogeneous cavity, including cavities through which objects can travel. Light-reflective structures 682 and 684, together with the region between them, can operate as an optical cavity when illuminated by input light, represented by arrows 686.

Structures 682 and 684 have electrodes 690 on their inward surfaces, facing each other and with elastically deformable spacers 692 and 694, such as elastomer or other deformable material, between them. As a result, signals can be provided to electrodes 690 to cause changes in distances between structures 682 and 684, changing the shape of the region between them, as suggested by angle 696. At positions where photon energy of input light is the same as a transmission mode of device 680, light is transmitted to photosensing component 698, which obtains sensing results. If analyte is present in the region between structures 682 and 684, optical cavity operation can provide analyte-affected output light. By independently addressing the electrodes on different spacers, it is also possible to keep a transmission mode's position unchanged while a neighboring mode moves further away or outside of the area of a photosensing device. This suggests how sensitivity and wavelength band can be chosen independently.

Figure 22:
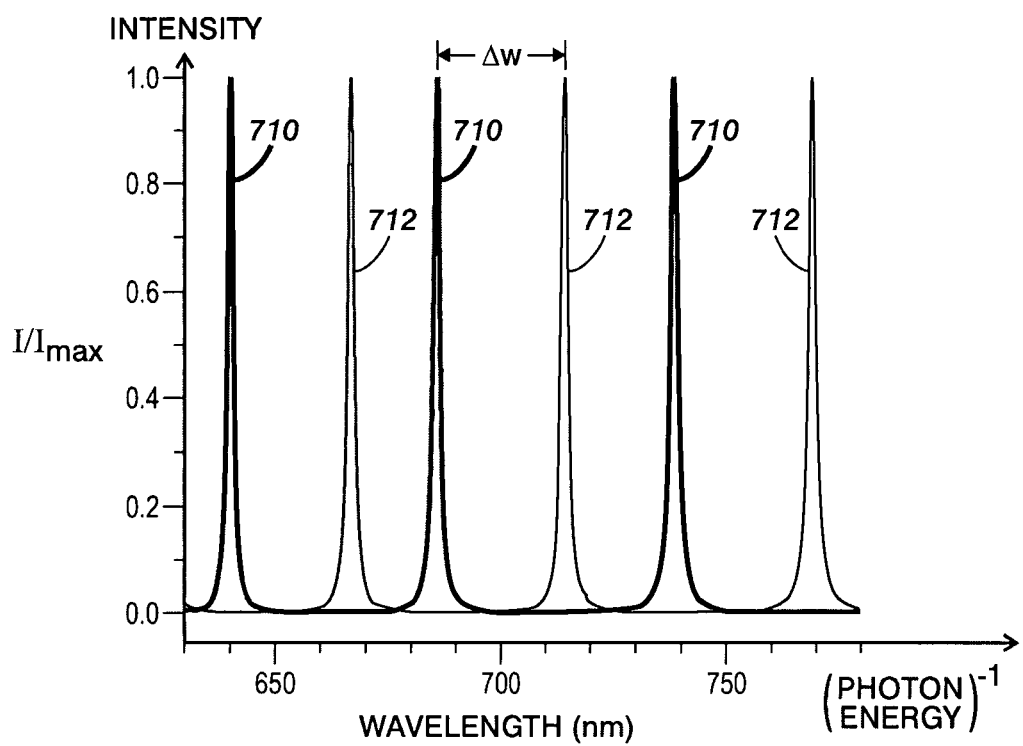
FIG. 22 is a graph showing two transmission spectra that could be provided by tuning an optical cavity as in FIG. 21.

FIG. 22 illustrates an example of how device 680 can be adjusted to obtain two different transmission spectra. The intensity-energy graph in FIG. 22 includes two curves: The curve that includes peaks 710 results from a spacing of 4.8 microns between structures 682 and 684, while the curve that includes peaks 712 results from a spacing of 5 microns. Although these curves indicate operation of device 680 as a homogeneous optical cavity, similar results would occur if it were operated as an inhomogeneous cavity as illustrated in FIG. 21, though an intensity-position graph would be more appropriate in that case. In either case, the output light could include information about optical characteristics of analyte in the region between structures 682 and 684, encoded as described above in relation to FIGS. 3 and 5.

Adjustments as in FIG. 22 can be performed at different intervals with device 680 to vary the absorption sampling points as in FIG. 13. For greater resolution of an absorption spectrum, for example, the number of sampling points can be increased, and it is in principle possible to continuously vary the thickness or tilt to obtain a continuous spectrum. Furthermore, a derivative, such as of absorption, can be directly measured by recording mode intensity while continuously changing cavity thickness; sensitivity of this technique can be further increased if the thickness is periodically modulated with a small amplitude (wobble) during the continuous change of cavity thickness.

The techniques in FIGS. 21 and 22 can also be extended to obtain derivatives by calculating slope between measurements of absorption or other optical characteristics at pairs of incrementally different photon energies obtained by tuning a homogeneous optical cavity that contains analyte. Similarly, cavity shape can be adjusted by such techniques to improve sensitivity.

A device as in FIG. 21 can also be used for other purposes, such as to produce an optical cavity or transmission structure with desired characteristics. For example, a homogeneous or inhomogeneous optical cavity with desired optical thickness could be produced; similarly, a transmission structure that is an LVF with a desired gradient could be produced.

Tunable cavities that can be inhomogeneous or that can contain analyte could be implemented in many ways besides the way illustrated in relation to FIGS. 21 and 22. Additional techniques are described, for example, in co-pending U.S. patent application Ser. No. 11/702,321, entitled "Tuning Optical Cavities" and in co-pending U.S. patent application Ser. No. 11/702,320, entitled "Tuning Optical Cavities", both of which are incorporated by reference herein in their entireties. In general, an optical cavity structure as in FIGS. 1 and 7 could be implemented to include one or more tunable cavities as in FIGS. 19-20.

Figure 23:
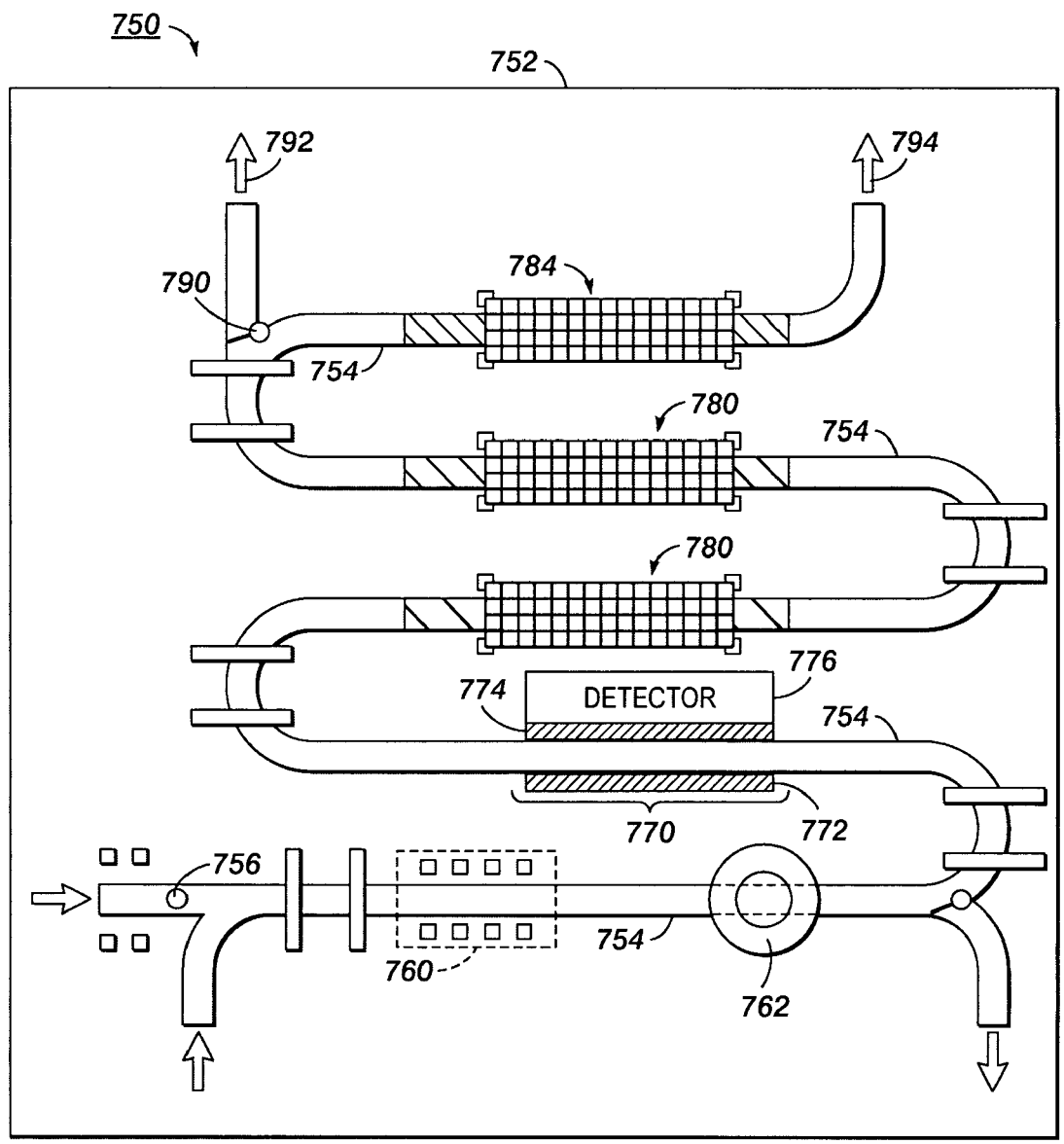
FIG. 23 is a schematic diagram of an analyzer on a fluidic structure, where the analyzer includes a system implemented as in FIGS. 7 and 8.

FIG. 23 illustrates an application of a system as in FIGS. 7 and 8 in analyzer 750 on support structure 752, a fluidic structure. Defined in support structure 752 is serpentine channel 754 through which object 756 can travel, carried by a fluid or other appropriate substance. Object 756 can, for example, be a droplet or a small volume of fluid that includes an analyte to be analyzed.

The manner in which object 756 enters channel 754 and is carried by fluid can be the same as described in co-pending U.S. patent application Ser. No. 11/315,386, entitled "Sensing Photon Energies Emanating from Channels or Moving Objects" and incorporated herein by reference in its entirety. As explained there, object 756 can be carried through channel 754 by operation of propulsion components and can be purged or otherwise caused to exit, together with fluid that is carrying it, from one of several outlets, such as through toggling of valves. While in channel 754, object 756 can travel through a series of sensing components, each of which can obtain information about object 756.

The first two sensing components after object 756 enters channel 754 are illustratively Coulter counter 760, an electrically based particle size detector, and Mie scatter sensor 762, also a particle size detector. As mentioned above, information about size of object 756 can be used in obtaining information about its optical characteristics, and this information can be obtained from Coulter counter 760 and Mie scatter sensor 762.

The next sensing component along channel 754 is optical cavity sensor 770, shown schematically in a cross-sectional view similar to that of FIG. 11, although it would typically be implemented instead with components above and below channel 754, similarly to other sensing components described below. The schematic illustration of sensor 770 includes light-reflective components 772 and 774 and detector 776, all of which might be implemented in a variety of ways, including some of those described above. In addition, one or more light sources (not shown) could illuminate the optical cavity.

After passing through sensor 770, particle 756 can continue through subsequent sensing components, illustratively including components 782 and 784. These could, for example, include first and second fluorescence sensing components and a Raman scatter sensing component. Information obtained from any combination of the sensing components can be used to distinguish between types of objects, such as different types of biological cells, or to distinguish objects from environment or background. Based on such a distinction, valve 790 at a bifurcation junction can be toggled between two positions, with object 756 exiting as indicating by arrow 792 if valve 790 is in one position and exiting as indicated by arrow 794 if value 790 is in another position.

Figure 24:
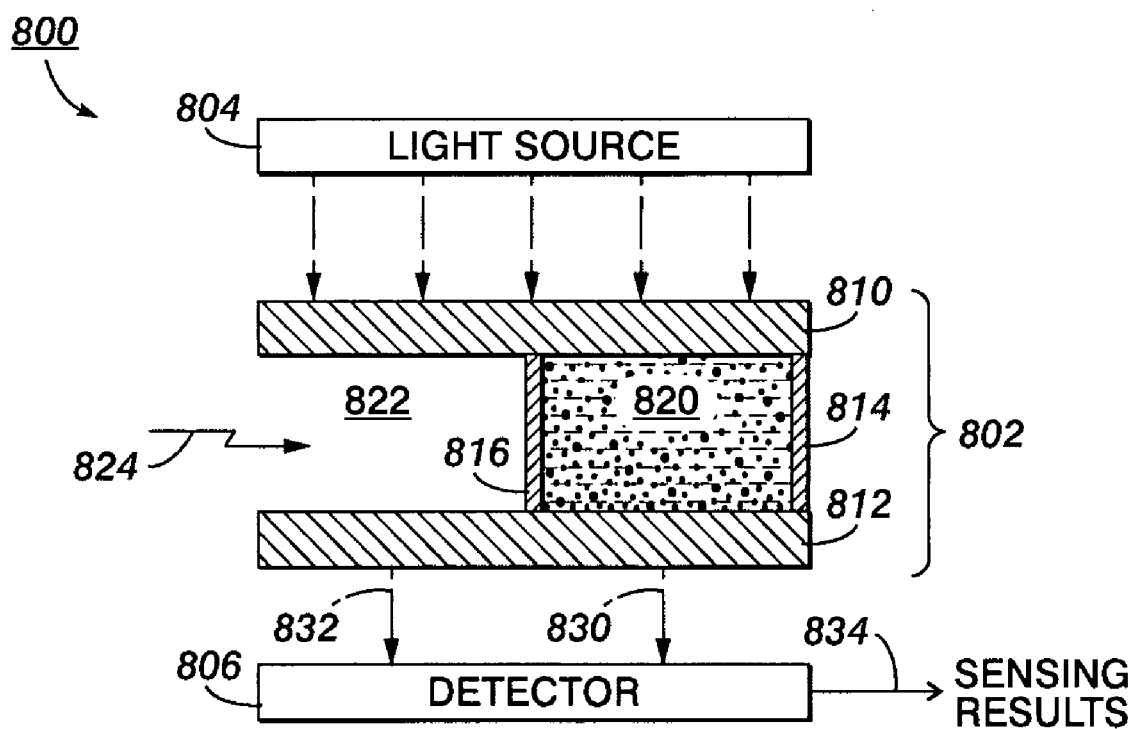
FIG. 24 is a schematic diagram of an implementation of a system as in FIG. 7 and 8 that can monitor analyte in bodily fluid.

FIG. 24 illustrates another application of a system as described above in relation to FIGS. 7 and 8. System 800 illustratively includes three components, various combinations of which could be feasibly implemented. Optical cavity component 802 receives input light from light source component 804 and, in turn, provides its output light to detector component 806. In the illustrated example, optical cavity component 802 is shown in cross-sectional view, showing how light-reflective structures 810 and 812 and wall structures 814 and 816 define two regions between light-reflective structures 810 and 812. Region 820, bounded by structures 810, 812, 814, and 816, can contain a reference fluid, while region 822, also bounded by structures 810, 812, and 816 but open at a side opposite wall structure 816, can contain fluid that enters as indicated by arrow 824.

In operation, analyte-carrying fluid, such as blood, lymph, interstitial fluid from between the cells of a human's or other organism's body, or other bodily fluid, can enter region 822 through any appropriate physical process; the analyte can be glucose, for example. As a result, optical cavity component 802 in effect operates as two parallel optical cavities: One optical cavity includes region 820 and provides output light, represented by arrow 830, with information about optical characteristics of the reference fluid (e.g. interstitial fluid with a well-known concentration); the other optical cavity includes region 822 and provides output light, represented by arrow 832, with information about a sample of fluid in which the analyte may be present. Detector 806 obtains sensing results that include both types of information and the sensing results can be provided to an external component such as a CPU or other processor, as indicated by arrow 834.

System 800 could be implemented in many different ways, and can include various optical cavity components, light sources, and detectors, including some of those described above. In addition to wristwatch-like implementations in which interstitial fluid is brought to the skin surface through small tubes or pins and then positioned in region 822, such as in one of the ways described above in relation to FIG. 1, several other implementations of system 800 using implantable products are described in co-pending U.S. patent application Ser. No. 11/702,329, entitled "Implanting Optical Cavity Structures" and incorporated herein by reference in its entirety.

Some of the implementations described above in relation to FIGS. 1-24 illustrate examples of a method in which objects travel through an optical cavity while the cavity is illuminated to provide output light. The objects affect the output light, which has a laterally varying intensity function that includes information about the objects. The method photosenses the output light to obtain sensing results that depend on the laterally varying intensity function, and also uses the sensing results to distinguish at least one of the objects.

In specific implementations, the method also controls the manner in which the objects travel through the optical cavity. In photosensing the output light, the method can receive the output light on a photosensitive surface at which the laterally varying intensity function affects the output light's position, and the sensing results can depend on that position. The method can use the sensing results, for example, in locating, counting, sorting, selecting, directing, separating, and determining paths of objects.

In further specific implementations, the objects can include two or more types, with objects of each type affecting the output light differently, and the method can distinguish at least one of the objects from one or more objects of other types. The objects can, for example, be biological cells, and the types can include a type of cancer cells and a type of non-cancer cells that the method distinguishes from each other. Or the types could include a type of rare cells, and the method could distinguish the rare cells. The method could also measure sizes of objects that travel through the optical cavity, and the sensing results could be used with the measured sizes to distinguish one of the objects from objects of other types.

In further specific implementations, the sensing results could be used to obtain information about at least one of refractive index and absorption of an object. Also, the laterally varying intensity function could include one or more peaks, and the sensing results could be used to detect a change in a feature of the laterally varying intensity function, such as in a central value, maximum intensity, contrast, or an intermediate intensity width of a peak. The sensing results could also be used to track one or more of the objects to obtain position data indicating its position. Tracking could include measuring a flow velocity of a medium through the cavity and using the sensing results and the measured flow velocity to track the objects.

Some of the implementations described above in relation to FIGS. 1-24 illustrate examples of a system that includes an optical cavity component with an optical cavity through which objects travel and affect output light, as described above. The system also includes a light source component that illuminates the optical cavity, a photosensing component that photosenses the output light to obtain sensing results that depend on the laterally varying intensity function, and an object distinguishing component that uses the sensing results to distinguish at least one of the objects.

In specific implementations, the optical cavity can be a homogeneous or inhomogeneous transmissive cavity. The optical cavity can provide output light in a mode with the mode's respective intensity function having a respective intensity peak. The modes can, for example, be transmission modes or reflection modes. The intensity function can include information about an optical characteristic of objects.

In further specific implementations, the photosensing component can be a photosensing array or a position-sensitive detector. If it includes an array that includes photosensing cells, the cells can be sized so that output light that includes information about one of the objects is concurrently photosensed by a set of two or more cells of an array. The object distinguishing component can include processing circuitry connected to receive the sensing results.

Some of the implementations described above in relation to FIGS. 1-24 also illustrate examples of a method of using optical cavities in which, while objects travel through an optical cavity in a medium, the cavity is operated to provide output light. Objects of one or more trackable types affect the output light so that it is different than the cavity would provide if no objects were in the medium. The output light has a varying intensity function while the objects travel through the cavity. The method photosenses the output light to obtain sensing results that depend on the varying intensity function, and uses the sensing results to track a set of the objects and to distinguish at least one of the tracked objects.

In specific implementations, the cavity can be illuminated to cause it to provide output light. Also, the sensing results can be used in locating, counting, sorting, selecting, directing, separating, and determining paths of objects.

In further specific implementations, the objects can include biological cells. The types can, for example, include a type of cancer cells and a type of non-cancer cells.

In further specific implementations, the method can measure sizes of objects and use the sensing results and the measured sizes to distinguish at least one of the tracked objects. The sensing results can be used, for example, to obtain information about at least one of refractive index and absorption of a tracked object, to detect a photon energy shift, or to obtain position data indicating an object's position.

In further specific implementations, the method can measure a flow velocity of the medium and use the sensing results and the measured flow velocity to track each tracked object. The medium with the objects can follow a path through the cavity, and the output light can be photosensed at a series of positions along the path, with photosensing performed at each position for a respective subrange of photon energies; the sensing results from each position can then be used to obtain information about an optical characteristic in the respective subrange. The medium with objects can concurrently follow two or more paths through the cavity, and photosensing of output light can be concurrently performed along each path, with the sensing results from more than one of the paths being used to distinguish at least one of the tracked objects.

In further specific implementations, photosensing can be performed with one or more arrays of photosensing cells, with the cells sized so that output light including information about one of the objects is concurrently photosensed by a set of two or more cells of one of the arrays. The sensing results for the set of cells can be combined.

The implementations in FIGS. 1-24 illustrate various applications of techniques as described above, including operating an optical cavity to provide object-encoded output light, such as with information about each object's refractive index and absorption coefficient, and using sensing results from photosensing the output light to distinguish objects.

Techniques that encode information about objects, as exemplified by the implementations in FIGS. 1-24, can be applied in many biochip and lab-on-chip devices and in micro total analysis systems, in which a compact unit able to measure optical characteristics of objects such as biological cells or particles used in fabrication or chemical processes with high accuracy would be highly desirable. Information about refractive index and absorption, for example, could be valuable in controlling a fabrication process or a chemical reaction, for example; the controlled chemical reaction could possibly occur inside the optical cavity, allowing measurement of refractive indices and absorption coefficients even of transitory objects resulting from the reaction. Refractive index and/or absorption index could be criteria used to make process control decisions, or could be used in a multivariable analysis, including one or more other types of information such as fluorescence or impedance.

Refractive index and absorption might be especially valuable for biological and biomedical applications. For example, the techniques described above could be used to measure optical properties (refractive index, dispersion, scattering, and absorption values) of single living cells in real time without extra treatment. Similarly, the techniques could be used to measure absorption coefficient and derivative to detect glucose or other analytes in bodily fluids, such as by using an implantable product. The techniques could also be implemented in a sophisticated fluidic system, as in flow cytometry and cell sorting systems, to count, sort, separate, select, or otherwise distinguish living cells of different types that are in a medium. For example, cancerous and non-cancerous cells could be counted and/or sorted.

The techniques could be applied not only to read out biochips or as part of a complex analysis system with fluidic or aerosol channels, but also in various other applications. They can be used, for example, in fluidic sample sensing, gas sensing, aerosol sensing, and so forth.

Various of the techniques described above have been successfully implemented or simulated, including the production and operation of a highly sensitive detector that includes a commercially available IC covered with a laterally graded Fabry-Perot cavity filter on a glass slide, and that can detect, for example, wavelength shift. Changes of laser and Fabry-Perot mode intensity peaks to indicate analyte optical characteristics have been simulated.

The exemplary implementations described above allow compact, inexpensive components to rapidly and accurately perform operations such as measuring optical characteristics of fluids, biological cells, glucose, and other analytes. In general, the techniques can be implemented in existing sensors and photosensors.

The exemplary implementations described above employ optical cavities with specific parameters and modes, but a wide variety of cavities could be used. Cavities with widths in the range from a few μm to hundreds of μm are feasible, and photon energies ranging from the ultraviolet up to the far infrared could be sampled.

In addition, components could have various shapes, dimensions, or other numerical or qualitative characteristics other than those illustrated and described above. For example, in some exemplary implementations described above, cells of a photosensor array photosense in different subranges of an application's photon energy range. The subranges of cells could have any appropriate widths and relationships, and could, for example, overlap or be distinct. The width of a cell's subrange can be chosen by designing the transmission structure and the cell sensing area; for example, the width may be as small as 0.1 nm or as great as tens of nanometers.

Some of the above exemplary implementations involve specific materials, such as in optical cavities and their components, but the invention could be implemented with a wide variety of materials and with layered structures with various combinations of sublayers.

Similarly, optical cavities could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in transmission structures may vary from 30 nm up to a few hundred nanometers.

Some of the above exemplary implementations could involve particular types of optical cavities, such as Bragg mirrors and paired distributed Bragg reflectors separated by a Fabry-Perot cavity, but, more generally, any appropriate optical cavity could be used to encode object optical characteristics. Various techniques could be used to produce optical cavities in addition to those described above, including, during deposition, tilting the substrate, using a shadow mask, or using a temperature gradient to obtain graded layer thickness; also, during homogeneous deposition, off-axis doping, such as by e-beam, MBE, or MOVPE, could produce lateral variation.

Some of the above exemplary implementations use specific lasers or other light sources to obtain light with desired characteristics, but various other light source techniques could be used within the scope of the invention. Various propagation components that propagate light between other components could also be employed.

The exemplary implementation in FIGS. 8 and 9 employs a CPU, which could be a microprocessor or any other appropriate component. Furthermore, as noted above, adjustment, combining, and other operations on photosensed quantities could be done either digitally or with analog signals, and could be done either on the same IC as a photosensor array, on other components, or on a combination of the two, with any appropriate combination of software or hardware.

The above exemplary implementations generally involve production and/or use of optical cavities, light sources, object distinguishing components, processing circuitry, and control circuitry following particular operations, but different operations could be performed, the order of the operations could be modified, and additional operations could be added within the scope of the invention. Also, readout of adjusted or unadjusted photosensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A method of using apparatus that includes an optical cavity component and a photosensing component; the optical cavity component including a light-transmissive region that is partially bounded by first and second light-reflective components such that the light-transmissive region is operable in response to illumination as an optical cavity in which constructive interference occurs in one or more photon energy subranges and destructive interference occurs in other photon energy subranges and that provides output light; each of the first and second light-reflective components having a respective reflection surface toward the light-transmissive region, the respective reflection surfaces being approximately parallel, the light-transmissive region including positions through which, in operation, objects travel in lateral directions approximately parallel to the reflection surfaces; the photosensing component receiving output light from the optical cavity; the method comprising:

while objects travel through the light-transmissive region, illuminating the light-transmissive region to operate as an optical cavity in which constructive interference occurs in one or more photon energy subranges and destructive interference occurs in other photon energy subranges, the optical cavity providing output light; the objects traveling through the light-transmissive region in lateral directions approximately parallel to the reflection surfaces; the objects affecting the output light, the output light having a laterally varying intensity function that includes information about the objects while the objects travel through the light-transmissive region;

photosensing the output light with the photosensing component to obtain sensing results that depend on the laterally varying intensity function; and using the sensing results to distinguish at least one of the objects.

2. The method of claim 1, further comprising:
controlling the manner in which the objects travel through the light-transmissive region.

3. The method of claim 1 in which the act of photosensing the output light comprises:
receiving the output light on a photosensitive surface, the laterally varying intensity function affecting the output light's position on the photosensitive surface; the sensing results depending on the output light's position.

4. The method of claim 1 in which the act of using the sensing results comprises at least one of locating, counting, sorting, selecting, directing, separating, and determining paths of objects.

5. The method of claim 1 in which the objects include two or more types and objects of each type affect the output light differently than objects of other types affect it; the act of using the sensing results comprising:
  distinguishing at least one of the objects from one or more objects of other types.

6. The method of claim 5 in which the objects include biological cells.

7. The method of claim 6 in which the two or more types include a type of cancer cells and a type of non-cancer cells; the method further comprising distinguishing cancer cells from non-cancer cells.

8. The method of claim 6 in which the two or more types include a type of rare cells; the method further comprising distinguishing rare cells.

9. The method of claim 5, further comprising:
  measuring sizes of objects that travel through the light-transmissive region;
  the act of using the sensing results comprising:
  using the sensing results and the measured sizes to distinguish at least one of the objects from one or more objects of other types.

10. The method of claim 1 in which the act of using the sensing results comprises:
  using the sensing results to obtain information about at least one of refractive index and absorption of an object.

11. The method of claim 1 in which the laterally varying intensity function includes one or more peaks, the act of using the sensing results comprises:
  using the sensing results to detect a change in a feature of the laterally varying intensity function.

12. The method of claim 11 in which the feature is one of a central value, a maximum intensity, a contrast, and an intermediate intensity width of at least one of the peaks.

13. The method of claim 1 in which the act of using the sensing results comprises:
  tracking one or more of the objects by using the sensing results to obtain position data indicating the tracked object's position.

14. The method of claim 13 in which the act of tracking one or more of the objects comprises:
  measuring a flow velocity of a medium through the light-transmissive region;
  using the sensing results and the measured flow velocity to track one or more of the objects.

15. A system comprising:
  an optical cavity component that includes a light-transmissive region that is partially bounded by first and second light-reflective components such that the light-transmissive region is operable in response to illumination as an optical cavity in which constructive interference occurs in one or more photon energy subranges and destructive interference occurs in other photon energy subranges and which provides output light; each of the first and second light-reflective components having a respective reflection surface toward the light-transmissive region, the respective reflection surfaces being approximately parallel; the light-transmissive region including positions through which, in operation, objects travel in lateral directions approximately parallel to the reflection surfaces, the objects affecting the output light, the output light having a laterally varying intensity function that includes information about the objects while the objects travel through the light-transmissive region;
  a light source component that, in operation, illuminates the light-transmissive region so that it operates as an optical cavity;
  a photosensing component that photosenses the output light to obtain sensing results that depend on the laterally varying intensity function; and
  an object distinguishing component that uses the sensing results to distinguish at least one of the objects.

16. The system of claim 15 in which the optical cavity is one of a homogeneous or inhomogeneous transmissive cavity.

17. The system of claim 15 in which the optical cavity provides output light in a mode with the mode's respective intensity function having a respective intensity peak.

18. The system of claim 17 in which the cavity is a transmissive cavity; the modes being transmission modes or reflection modes.

19. The system of claim 18 in which the intensity function of each of the at least one of the modes includes information about an optical characteristic of one or more objects traveling through the optical cavity.

20. The system of claim 15 in which the photosensing component is one of a photosensing array or a position-sensitive detector.

21. The system of claim 20 in which the photosensing component includes one or more arrays that include photosensing cells, the photosensing cells of at least one of the arrays being sized so that output light that includes information about one of the objects is concurrently photosensed by a set of two or more of the photosensing cells of one of the arrays.

22. The system of claim 15 in which the object distinguishing component includes processing circuitry connected to receive the sensing results from the photosensing component.

23. The system of claim 15 in which, in operation, objects travel through the light-transmissive region in at least one of the following:
  in a medium;
  carried by a fluid;
  through a porous material;
  due to a difference in momentum;
  due to a difference in density;
  due to an electric charge;
  due to a magnetic characteristic; and
  due to self-propulsion.

24. A method of using apparatus that includes an optical cavity component and a photosensing component; the optical cavity component including a light-transmissive region that is operable as a transmissive optical cavity; the photosensing component receiving output light from the optical cavity; the method comprising:
  while objects travel through the light transmissive region, illuminating the light-transmissive region; in response, the light-transmissive region operating as a transmissive optical cavity that provides output light; the objects affecting the output light, the output light having a laterally varying intensity function that includes information about the objects while the objects travel through the light-transmissive region;
  with the photosensing component, photosensing the output light to obtain sensing results that depend on the laterally varying intensity function, the sensing results including information about the objects; and
  using the sensing results to distinguish at least one of the objects; the act of using the sensing results comprising:
  using the information about the objects to distinguish at least one of the objects.

25. A system comprising:
  an optical cavity component that includes a light-transmissive region through which objects travel, the light-transmissive region being operable as a transmissive optical cavity that provides output light in response to illumination, the objects affecting the output light, the output light having a laterally varying intensity function that includes information about the objects while the objects travel through the cavity;

a light source component that illuminates the light-transmissive region so that it operates as the transmissive optical cavity and provides the output light having the laterally varying intensity function;

a photosensing component that photosenses the output light to obtain sensing results that depend on the laterally varying intensity function, the sensing results including information about the objects; and an object distinguishing component that uses the sensing results, the object distinguishing component using the information about the objects to distinguish at least one of the objects.

26. A method of using apparatus that includes an optical cavity component and a photosensing component; the optical cavity component including a light-transmissive region that is operable as an optical cavity; the photosensing component receiving output light from the optical cavity; the method comprising:

while objects travel through the light-transmissive region in a medium, operating the light-transmissive region as an optical cavity that provides output light; objects of one or more trackable types affecting output light provided by the cavity so that it is different than the cavity would provide if no objects were in the medium; the output light having a varying intensity function while the objects travel through the cavity; the varying intensity function including information about the objects of the trackable types;

with the photosensing component, photosensing the output light to obtain sensing results that depend on the varying intensity function, the sensing results including information about the objects of the trackable types; and using the sensing results to track a set of the objects of the trackable types and to distinguish at least one of the tracked objects; the act of using the sensing results comprising:

using the information about the objects of the trackable types to distinguish at least one of the tracked objects.

27. A method of using apparatus that includes an optical cavity component and a photosensing component; the optical cavity component including a light-transmissive region that is partially bounded by first and second light-reflective components such that the light-transmissive region is operable as an optical cavity that provides output light; each of the first and second light-reflective components having a respective reflection surface toward the light-transmissive region, the respective reflection surfaces being approximately parallel; the photosensing component receiving output light from the optical cavity; the method comprising:

while objects travel through the light-transmissive region in a medium, operating the light-transmissive region as an optical cavity in which constructive interference occurs in one or more photon energy subranges and destructive interference occurs in other photon energy subranges, the optical cavity providing output light; the objects traveling through the light-transmissive region in lateral directions approximately parallel to the reflection surfaces; objects of one or more trackable types affecting output light provided by the cavity so that it is different than the cavity would provide if no objects were in the medium; the output light having a varying intensity function that includes information about the objects while the objects travel through the light-transmissive region;

photosensing the output light with the photosensing component to obtain sensing results that depend on the varying intensity function; and using the sensing results to track a set of the objects of the trackable types and to distinguish at least one of the tracked objects.

28. The method of claim 27 in which the objects include biological cells.

29. The method of claim 28 in which the one or more types include a type of cancer cells and a type of non-cancer cells.

30. The method of claim 27, further comprising:

measuring sizes of objects in the set;

the act of using the sensing results comprising:

using the sensing results and the measured sizes to distinguish at least one of the tracked objects.

31. The method of claim 27 in which the act of using the sensing results comprises:

using the sensing results to obtain information about at least one of refractive index and absorption of a tracked object.

32. The method of claim 27 in which the act of using the sensing results comprises:

using the sensing results to detect a photon energy shift.

33. The method of claim 27 in which the act of using the sensing results comprises:

tracking each tracked object by using the sensing results to obtain position data indicating the tracked object's position.

34. The method of claim 27, further comprising:

measuring a flow velocity of the medium through the light-transmissive region;

the act of using the sensing results comprising:

using the sensing results and the measured flow velocity to track each tracked object.

35. The method of claim 27 in which the medium with the objects follows a path through the light-transmissive region, the act of photosensing the output light comprising:

photosensing at a series of positions along the path, with photosensing being performed at each position for a respective subrange of photon energies;

the act of using the sensing results comprising:

using the sensing results from each position to obtain information about an optical characteristic in the respective subrange of photon energies.

36. The method of claim 27 in which the medium with the objects concurrently follows two or more paths through the light-transmissive region, the act of photosensing the output light comprising:

concurrently photosensing along each path;

the act of using the sensing results comprising:

using the sensing results from more than one of the paths to distinguish at least one of the tracked objects.

37. A method of using apparatus that includes an optical cavity component and a photosensing component; the optical cavity component including a light-transmissive region that is operable as an optical cavity that provides output light; the photosensing component receiving output light from the optical cavity; the method comprising:

while objects travel through the light-transmissive region, operating the light-transmissive region as an optical cavity that provides output light; each of the objects having an absorption characteristic and/or a refractive index characteristic; the objects affecting the output light, the output light having a varying intensity function that is affected by each object's absorption characteristic and/or refractive index characteristic while the object travels through the light-transmissive region;

photosensing the output light to obtain sensing results that include information about each object's absorption characteristic and/or refractive index characteristic; and using the sensing results to distinguish at least one of the objects; the act of using the sensing results comprising:

using the information about absorption characteristic and/or refractive index characteristic to distinguish at least one of the objects;

the cavity being one of:
(1) a transmissive cavity, illuminated to provide output light with the varying intensity function, wherein at least one of:
(a) the varying intensity function is a laterally varying intensity function; and
(b) the sensing results are used to track a set of the objects that are of one or more trackable types; the information about absorption characteristic and/or refractive index characteristic being used to distinguish at least one of the tracked objects; and
(2) an emitting cavity operated to provide output light with the varying intensity function; the objects being of one or more trackable types; the sensing results being used to track a set of the objects of the trackable types; the information about absorption characteristic and/or refractive index characteristic being used to distinguish at least one of the tracked objects.

38. The method of claim 37 in which the varying intensity function is one of:
an intensity-energy function, different lateral positions having different intensity-energy functions; and
an intensity-position function, different lateral positions having different intensities.

39. The method of claim 37 in which the varying intensity function includes modes, the information about absorption characteristic and/or refractive index characteristic including at least one of:
information about a mode's central energy;
information about shift of a mode's central energy;
information about a mode's intensity amplitude;
information about a mode's intermediate intensity width;
information about a mode's contrast;
information about absorption spectra; and
information about refractive index dispersion.

* * * * *